US009461250B2

(12) United States Patent
Ogawa et al.

(10) Patent No.: US 9,461,250 B2
(45) Date of Patent: Oct. 4, 2016

(54) ORGANIC ELECTROLUMINESCENT DEVICE

(75) Inventors: Junya Ogawa, Kitakyushu (JP);
Takahiro Kai, Kitakyushu (JP);
Toshihiro Yamamoto, Kitakyushu (JP);
Megumi Matsumoto, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 170 days.

(21) Appl. No.: 13/514,047

(22) PCT Filed: Dec. 21, 2010

(86) PCT No.: PCT/JP2010/073022
§ 371 (c)(1),
(2), (4) Date: Jun. 5, 2012

(87) PCT Pub. No.: WO2011/081061
PCT Pub. Date: Jul. 7, 2011

(65) Prior Publication Data
US 2012/0235136 A1 Sep. 20, 2012

(30) Foreign Application Priority Data
Dec. 28, 2009 (JP) .................. 2009-297902

(51) Int. Cl.
*H01L 51/50* (2006.01)
*H01L 51/00* (2006.01)
(Continued)

(52) U.S. Cl.
CPC ......... *H01L 51/0072* (2013.01); *C07D 209/86* (2013.01); *C07D 209/88* (2013.01); *C07D 409/14* (2013.01); *C09K 11/06* (2013.01); *C09K 2211/1029* (2013.01);
(Continued)

(58) Field of Classification Search
None
See application file for complete search history.

(56) References Cited

U.S. PATENT DOCUMENTS

2002/0034656 A1* 3/2002 Thompson et al. .......... 428/690
2003/0221763 A1* 12/2003 Tateishi et al. ................. 156/67
(Continued)

FOREIGN PATENT DOCUMENTS

CN 101126020 A 2/2008
CN 101139317 A 3/2008
(Continued)

OTHER PUBLICATIONS

Machine English translation of JP 2005-093159 A. Oct. 21, 2014.*
EPO machine English translation of Zeng et al. (CN 101126020 A). Apr. 11, 2015.*
(Continued)

Primary Examiner — J. L. Yang
(74) Attorney, Agent, or Firm — Cheng Law Group, PLLC

(57) ABSTRACT

Disclosed is an organic electroluminescent device (organic EL device) which is improved in luminous efficiency, sufficiently secures driving stability, and has a simple configuration. The organic EL device of this invention comprises a light-emitting layer between an anode and a cathode piled one upon another on a substrate wherein the light-emitting layer contains a phosphorescent dopant and a 1,9-substituted carbazole compound as a host material. An example of the 1,9-substituted carbazole compound is represented by the following general formula (1). In formula (1), Ar is an aromatic hydrocarbon group or aromatic heterocyclic group; L is an aromatic hydrocarbon group or aromatic heterocyclic group; each of $R_1$ to $R_3$ is a hydrogen atom, an alkyl group, a cycloalkyl group, an aromatic hydrocarbon group, or an aromatic heterocyclic group; n is an integer of 1 to 3.

4 Claims, 4 Drawing Sheets

(51) Int. Cl.
*C07D 209/86* (2006.01)
*C07D 209/88* (2006.01)
*C07D 409/14* (2006.01)
*C09K 11/06* (2006.01)

(52) U.S. Cl.
CPC ........... *C09K 2211/1088* (2013.01); *C09K 2211/1092* (2013.01); *H01L 51/0074* (2013.01); *H01L 51/0085* (2013.01); *H01L 51/5016* (2013.01)

(56) References Cited

U.S. PATENT DOCUMENTS

2007/0252521 A1* 11/2007 Kondakov et al. ........... 313/506
2009/0236973 A1* 9/2009 Yabe et al. ................... 313/504
2009/0284138 A1* 11/2009 Yasukawa et al. ........... 313/504

FOREIGN PATENT DOCUMENTS

| EP | 2 123 733 A2 | 11/2009 |
| JP | 2001-313178 A | 11/2001 |
| JP | 2003-515897 A | 5/2003 |
| JP | 2005-93159 A | 4/2005 |
| WO | WO-2009/086028 A2 | 7/2009 |

OTHER PUBLICATIONS

International Preliminary Report on Patentability for the Application No. PCI7JP2010/073022 mailed Sep. 20, 2012.
International Search Report for the Application No. PCT/JP2010/073022 mailed Mar. 15. 2011.
Holmes, R. J. et al., "Blue Organic Electrophosphorescence Using Exothermic Host-Guest Energy Transfer", Applied Physics Letters, 2003, vol. 82, No. 15, pp. 2422-2424.

* cited by examiner

ORGANIC ELECTROLUMINESCENT DEVICE

TECHNICAL FIELD

This invention relates to an organic electroluminescent device using a carbazole compound of a specified structure.

BACKGROUND TECHNOLOGY

An organic electroluminescent device (hereinafter referred to as organic EL device) in the simplest structure is generally constituted of a light-emitting layer and a pair of counter electrodes holding the light-emitting layer between them. The organic EL device functions by utilizing the following phenomenon; upon application of an electric field between the electrodes, electrons are injected from the cathode and holes are injected from the anode and they recombine in the light-emitting layer with emission of light.

In recent years, organic thin films have been utilized in the development of organic EL devices. In particular, in order to enhance the luminous efficiency, the kind of electrodes has been optimized for the purpose of improving the efficiency of injecting carriers from the electrodes and a device has been developed in which a hole-transporting layer composed of an aromatic diamine and a light-emitting layer composed of 8-hydroxyquinoline aluminum complex (Alq3) are disposed in thin film between the electrodes. This device has brought about a marked improvement in the luminous efficiency over the conventional devices utilizing single crystals of anthracene and the like and thereafter the developmental works of organic EL devices have been directed toward commercial applications to high-performance flat panels featuring self-luminescence and high-speed response.

Further, in an effort to enhance the luminous efficiency of the device, the use of phosphorescence in place of fluorescence is investigated. The aforementioned device comprising a hole-transporting layer composed of an aromatic diamine and a light-emitting layer composed of Alq3 and many others have utilized fluorescence. The use of phosphorescence, that is, emission of light from the triplet excited state, is expected to enhance the luminous efficiency three to four times that of the conventional devices using fluorescence (emission of light from the singlet excited state). To achieve this objective, the use of coumarin derivatives and benzophenone derivatives in the light-emitting layer was investigated, but these derivatives merely produced luminance at an extremely low level. Europium complexes were also investigated in trials to utilize the excited triplet state, but they failed to emit light at high efficiency. In recent years, as stated in patent document 1, a large number of researches are conducted on phosphorescent dopant materials with the objective of enhancing the luminous efficiency and extending the life while giving priority to utilization of organic metal complexes such as iridium complexes.

PRIOR ART TECHNICAL DOCUMENTS

Patent Documents

Patent document 1: JP 2003-515897 A
Patent document 2: JP 2001-313178 A
Patent document 3: WO 2009/086028
Patent document 4: JP 2005-093159 A
Patent document 5: CN101126020
Patent document 6: CN101139317

Non-Patent Documents

Non-patent document 1: Applied Physics Letters, 2003, 82, 2422-2424

In order to obtain high luminous efficiency, a host material to be used together with the aforementioned dopant material becomes important. Of the host materials proposed thus far, typical examples are 4,4'-bis(9-carbazolyl)biphenyl (hereinafter referred to as CBP), a carbazole compound presented in patent document 2, and 1,3-dicarbazolybenzene (hereinafter referred to as mCP) presented in non-patent document 1. Since CBP is characterized by having a good hole transfer property but a poor electron transfer property, the use of CBP as a host material for tris(2-phenylpyridine)iridium complex (hereinafter referred to as $Ir(ppy)_3$), a typical phosphorescent green light-emitting material, disturbs the balanced injection of charges and causes excessive holes to flow out to the side of the electron-transporting layer. The results is a reduction in the luminous efficiency of $Ir(ppy)_3$. On the other hand, mCP exhibits relatively good luminous characteristics when used as a host material for bis[2-(4,6-difluorophenyl)-pyridinato-N,C2'](picolinate) iridium complex (hereinafter referred to as FIrpic), a typical phosphorescent blue light-emitting material. However, mCP is not satisfactory for practical use particularly from the viewpoint of durability.

As described above, in order for an organic EL device to display high luminous efficiency, host materials which are well balanced in the characteristics relating to injection and transportation of electric charges (holes and electrons) are required. Among such host materials, those having higher triplet excited energy (hereinafter referred to as T1 energy) are preferred. Furthermore, compounds which are electrochemically stable, highly resistant to heat, and excellently stable in the amorphous state are desired and further improvements are demanded.

Patent document 3 discloses the carbazole compound shown below as a light-emitting material.

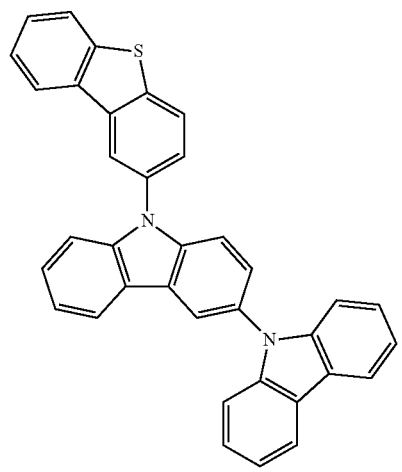 [SMILES: c1ccc2c(c1)sc1ccc(-n3c4ccccc4c4cc(-n5c6ccccc6c6ccccc65)ccc43)cc12]

In the aforementioned compound, the 9 position of the carbazole ring in the center has a dibenzothienyl group as a substituent, but the 1 position has no substituent and the 3 position has a carbazolyl group as a substituent. A structure such as this shows low stability against electric charges and is not suited for practical use.

Patent document 4 discloses the carbazole compound shown below as a light-emitting material.

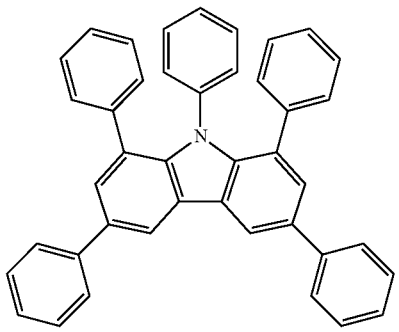 [SMILES: c1ccc(-c2cc(-c3ccccc3)c3c(c2)c2cc(-c4ccccc4)cc(-c4ccccc4)c2n3-c2ccccc2)cc1]

The aforementioned compound has phenyl groups as substituents at the 1 and 9 positions. This structure shows a poor balance of electric charges and does not provide sufficient luminous efficiency.

Further, patent document 5 discloses the carbazole compound shown below as a light-emitting material.

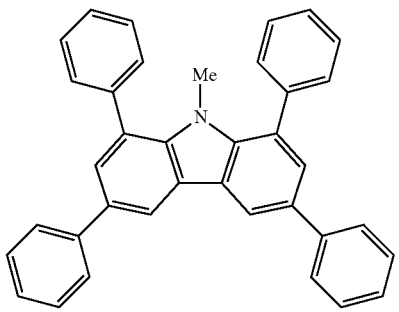 [SMILES: Cn1c2c(-c3ccccc3)cc(-c3ccccc3)cc2c2cc(-c3ccccc3)cc(-c3ccccc3)c21]

The aforementioned compound has a phenyl group at the 1 position and a methyl group at the 9 position. The presence of an alkyl group at the 9 position causes the conjugation to extend broadly and, as a result, the T1 energy decreases and sufficient luminous efficiency is not obtained. Moreover, an organic EL device using the aforementioned compound deteriorates markedly in durability because of the presence of an alkyl group at the 9 position.

Patent document 6 discloses the carbazole compound shown below as a light-emitting material.

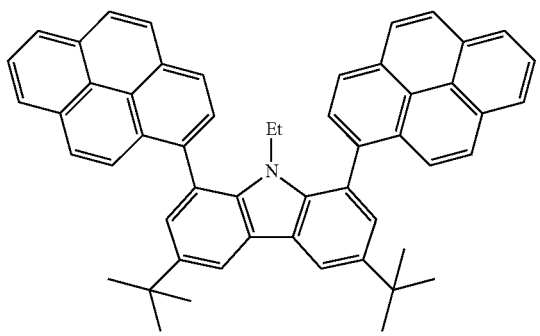 [SMILES: CCn1c2c(-c3ccc4ccc5cccc6ccc3c4c56)cc(C(C)(C)C)cc2c2cc(C(C)(C)C)cc(-c3ccc4ccc5cccc6ccc3c4c56)c21]

The aforementioned compound has a pyrenyl group, which is a fused aromatic group composed of more than two rings, at the 1 position. However, the presence of an alkyl group at the 9 position causes the conjugation to extend broadly and, as a result, the T1 energy decreases and sufficient luminous efficiency is not obtained. Moreover, an organic EL device using the aforementioned compound deteriorates markedly in durability because of the presence of an alkyl group at the 9 position.

As described above, patent document 3 discloses a carbazole compound having a fused aromatic group composed of two rings or more, but does not disclose a carbazole compound having substituents at both the neighboring 1 and 9 positions. Patent documents 4 to 6 disclose carbazole compounds having substituents at the 1 and 9 positions, either monocyclic aryl groups at the 1 and 9 positions or an alkyl group at the 9 position. Hence, these patent documents do not disclose a carbazole compound having aromatic groups, either one of which is a fused ring, at the 1 and 9 positions.

A large number of studies have been conducted on carbazole derivatives since they have excellent charge transfer properties and electrochemical stability as described above. However, they do not yet have characteristics satisfactory for practical use in phosphorescent light-emitting devices and there is a demand for further improvements.

SUMMARY OF THE INVENTION

In applications of organic EL devices to display devices such as flat panel displays, it is necessary to enhance the luminous efficiency of the device and, at the same time, to sufficiently secure the driving stability of the device. Under the aforementioned circumstances, an object of this invention is to provide an organic EL device exhibiting such luminous efficiency and driving stability as to be practically useful and to provide a compound suitable therefor.

The inventors of this invention have conducted intensive studies, found that the use of a carbazole compound having aromatic groups, at least one of which is a fused aromatic group, as substituents at the 1 and 9 positions as a material for a phosphorescent light-emitting device can display excellent characteristics, and completed this invention.

Accordingly, this invention relates to an organic electroluminescent device comprising an anode, a plurality of organic layers, and a cathode piled one upon another on a substrate wherein the plurality of organic layers comprise an organic layer containing a carbazole compound having aromatic groups selected from aromatic hydrocarbon groups and aromatic heterocyclic groups, at least one of the said aromatic groups having a fused ring structure composed of two rings or more, as substituents at the 1 and 9 positions and having the total of 20 to 80 carbon atoms as a material for a phosphorescent light-emitting device.

Preferable examples of the aforementioned carbazole compound are compounds represented by the following general formula (1) or (2).

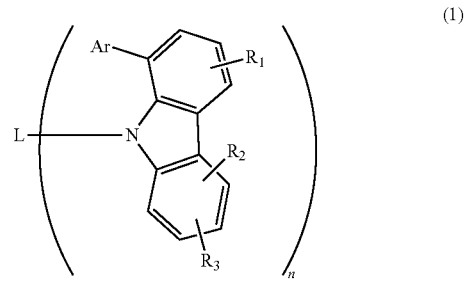

(1)

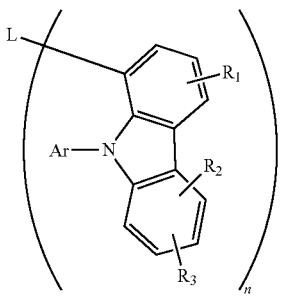

(2)

In general formulas (1) and (2), each Ar is independently an aromatic group selected from aromatic hydrocarbon groups of 6 to 24 carbon atoms and aromatic heterocyclic groups of 3 to 23 carbon atoms; L is an aromatic group selected from aromatic hydrocarbon groups of 6 to 30 carbon atoms and aromatic heterocyclic groups of 3 to 30 carbon atoms; each of $R_1$ to $R_3$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms; n is an integer of 1 to 3; when n is 2 or more, a plurality of Ar's or $R_1$ to $R_3$ may be identical with or different from one another; however, at least one of Ar and L is an aromatic group having a fused ring structure composed of 2 rings or more.

In general formula (1) or (2), it is preferable that one or both of Ar and L are derived, the former as a monovalent aromatic group and the latter as an n-valent aromatic group, from an aromatic compound represented by the following general formula (3).

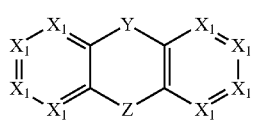

(3)

In general formula (3), each $X_1$ is independently $CR_4$ or a nitrogen atom; Y is —O—, —S—, or —$NR_5$—; Z is a direct bond, —O—, —S—, —$NR_6$—, —$CR_7R_8$—, or a group represented by the following formula (Z-1); each of $R_4$ to $R_8$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms; however, the aromatic group derived from a compound represented by general formula (3) is a monovalent aromatic group in case it is Ar or an n-valent aromatic group in case it is L.

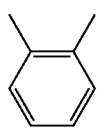

(Z-1)

In general formula (3), it is preferable that Z is a direct bond.

In general formula (1) or (2), it is equally preferable that either Ar or L is a monovalent or n-valent aromatic group derived from an aromatic compound represented by the following general formula (4).

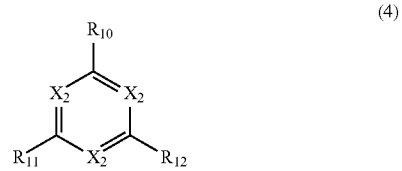

(4)

In general formula (4), each $X_2$ is independently $CR_9$ or a nitrogen atom; each of $R_9$ to $R_{12}$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms; however, the aromatic group derived from general formula (4) is a monovalent aromatic group in case it is Ar or an n-valent aromatic group in case it is L.

It is desirable that the organic layer containing a material for a phosphorescent light-emitting device is at least one layer selected from the group consisting of a light-emitting layer, a hole-transporting layer, an electron-transporting layer, and a hole-blocking layer. Further, it is desirable that the organic layer containing a material for a phosphorescent light-emitting device is a light-emitting layer containing a phosphorescent dopant. Still further, it is desirable that light emitted from the phosphorescent dopant has a peak wavelength in the range below 550 nm.

The 9 position of carbazole is known to have high electron density and show high reactivity: the hydrogen atom at the 9 position is active in the unsubstituted structure whereas the carbon and hydrogen atoms linked to the 9 position are active in an alkyl-substituted structure. The use of a carbazole compound either unsubstituted or alkyl-substituted at the 9 position in an organic EL device markedly deteriorates the durability. Therefore, in order to improve the durability of an organic EL device, it becomes essential to use a carbazole compound having an aromatic group as a substituent at the 9 position. Furthermore, substitution of the hydrogen atoms at the neighboring 1 and 9 positions of a carbazole compound with aromatic groups, at least one of which is a fused aromatic group composed of two rings or more, increases the strain of the carbazole skeleton and suppresses extension of the molecular orbitals distributed over respective substituents. The electrochemical stability (stability against oxidation or reduction) is closely related to the molecular orbitals contributing thereto (the highest occupied molecular orbital (HOMO) in oxidation and the lowest unoccupied molecular orbital (LUMO) in reduction) and, in order to improve the stability of the molecule itself against electric charges, it is absolutely necessary to design a molecule so that the HOMO is distributed in the part of high stability against oxidation and the LUMO is distributed in the part of high stability against reduction. It is conceivable that the aforementioned suppression of extension of the molecular orbital has the effect of distributing the molecular orbitals in the parts of high stability against oxidation and reduction and providing good stability against electric charges. It is further conceivable that an increase in the strain of the whole compound suppresses extension of the conjugation of the whole molecule and increases the energy. It is inferred that, due to the aforementioned effect, the carbazole compound to be used in this invention has good stability against electric charges and provides a phosphorescent host material of higher T1 energy.

The carbazole compound of this invention is thought to have an ability to adjust the barriers to injection of electric charges at lower levels by exercising the aforementioned control of extension of the molecular orbitals. Thus, incorporation of the carbazole compound of this invention as a phosphorescent light-emitting material in the light-emitting layer improves the balance of electric charges and the probability of their recombination. In short, an organic EL device using the said phosphorescent light-emitting material attains high luminous efficiency. In addition, the said material exhibits good characteristics in the amorphous state, high heat resistance, and electrochemical stability and realizes an organic EL device of long driving life and high durability.

PREFERRED EMBODIMENTS OF THE INVENTION

Figure 1:
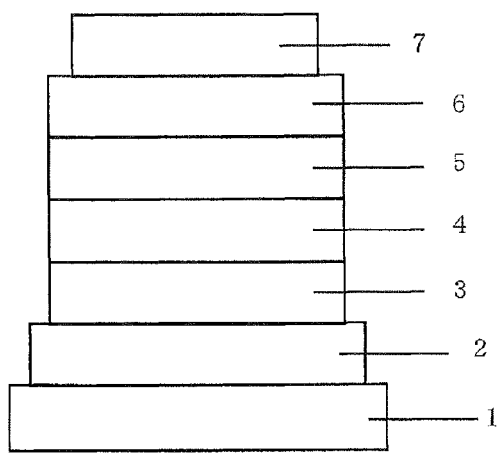
FIG. 1 shows the cross section of an example of an organic EL device.

The carbazole compound to be used in this invention has aromatic groups selected from aromatic hydrocarbon groups and aromatic heterocyclic groups as substituents at the 1 and 9 positions of the carbazole ring and at least one of the aromatic groups has a fused ring structure composed of two rings or more. The substituents at the 1 and 9 positions are aromatic groups and the aromatic groups here are meant to include aromatic hydrocarbon groups and aromatic heterocyclic groups. The carbazole compound to be used in this invention is hereinafter also referred to as a 1,9-substituted carbazole compound.

A preferable 1,9-substituted carbazole compound is represented by the aforementioned general formula (1) or (2). In general formulas (1) and (2), Ar is an aromatic group selected from aromatic hydrocarbon groups of 6 to 24 carbon atoms and aromatic heterocyclic groups of 3 to 23 carbon atoms. This aromatic group may or may not have a substituent.

Preferable examples of the aromatic groups having no substituent include monovalent aromatic groups formed by removing one hydrogen atom from benzene, pyridine, pyrimidine, triazine, furan, thiophene, naphthalene, fluorene, phenanthrene, anthracene, pyrene, indole, quinoline, isoquinoline, naphthyridine, quinoxaline, quinazoline, benzofuran, benzothiophene, carbazole, acridine, phenanthroline, phenothiazine, phenoxazine, dibenzofuran, dibenzothiophene, dibenzazepine, and tribenzazepine.

Preferable examples of aromatic groups having a substituent include aromatic groups obtained by replacing a hydrogen atom of the aforementioned aromatic groups having no substituent with a suitable substituent. Specific examples of the substituent include an alkyl group of 1 to 4 carbon atoms, an alkoxyl group of 1 to 2 carbon atoms, an acetyl group, an aryl group of 6 to 12 carbon atoms, and a heteroaryl group of 3 to 11 carbon atoms. More preferable examples include a phenyl group, a naphthyl group, a carbazolyl group, a quinolyl group, and an isoquinolyl group. In this specification, the number of carbon atoms in an aromatic group represented by Ar or L does not include the number of carbon atoms in a substituent. However, it is preferable that the number of carbon atoms in Ar or L remains in the aforementioned range even when the number of carbon atoms in a substituent is included. In the case where the carbazole compound in this invention has two or more carbazole rings in the molecule, at least one of the carbazole rings needs to have the aforementioned aromatic groups as substituents at the 1 and 9 positions. This particular carbazole ring is hereinafter referred to as the central carbazole ring. Further, the central carbazole ring may be substituted with carbazole at other position.

In general formulas (1) and (2), Ar is preferably a monovalent aromatic group derived from the aromatic compound represented by the aforementioned general formula (3) or (4). General formulas (3) and (4) will be explained additionally later on.

In general formulas (1) and (2), L is an aromatic group selected from aromatic hydrocarbon groups of 6 to 30 carbon atoms and aromatic heterocyclic groups of 3 to 30 carbon atoms. This aromatic group may or may not have a substituent.

Preferable examples of the aromatic groups having no substituent include n-valent groups formed by removing n number of hydrogen atoms from benzene, pyridine, pyrimidine, triazine, furan, thiophene, naphthalene, fluorene, phenanthrene, anthracene, pyrene, indole, quinoline, isoquinoline, naphthyridine, quinoxaline, quinazoline, benzofuran, benzothiophene, carbazole, acridine, phenanthroline, phenothiazine, phenoxazine, dibenzofuran, dibenzothiophene, dibenzazepine, and tribenzazepine.

Specific examples of aromatic groups having a substituent include aromatic groups obtained by replacing a hydrogen atom of the aforementioned aromatic groups having no substituent with a suitable substituent. Specific examples of the substituent include an alkyl group of 1 to 4 carbon atoms, an alkoxyl group of 1 to 2 carbon atoms, and an acetyl group. The aforementioned substituent may further have a substituent and preferable examples of such a substituent include an alkyl group of 1 to 4 carbon atoms, an alkoxyl group of 1 to 2 carbon atoms, an acetyl group, an aryl group of 6 to 12 carbon atoms, and a heteroaryl group of 3 to 11 carbon atoms. More preferable examples include a phenyl group, a naphthyl group, a carbazolyl group, a quinolyl group, and an isoquinolyl group.

Furthermore, Ar or L may be an aromatic group in which a plurality of the aforementioned aromatic groups having no substituent are linked together. In this case, the aromatic group in question may be regarded as a group consisting of an aromatic group which is linked to the central carbazole ring and other aromatic groups linked to the said aromatic group as substituents. Specific examples of such an aromatic group include monovalent or n-valent groups derived from biphenyl, terphenyl, bipyridine, bipyrimidine, phenylpyridine, diphenylpyridine, phenylpyrimidine, diphenylpyrimidine, phenyltriazine, diphenyltriazine, and phenylcarbazole.

In general formulas (1) and (2), substitution of L takes place at the 1 or 9 position of the central carbazole ring. When n is 2 or 3, L is linked to the central carbazole ring and also to other carbazole rings. The position of substitution at other carbazole rings is not limited and it may be on a terminal ring or a ring in the middle.

In general formulas (1) or (2), at least one of Ar and L is an aromatic group having a fused ring structure composed of two rings or more. Here, in the case where an aromatic group of a fused ring structure has a substituent, the aromatic group of a fused ring structure needs to be linked directly to the central carbazole ring and, in the case where the aromatic group of a fused ring structure has an aromatic group as a substituent, this substituent aromatic group may be a monocyclic ring. Preferably, at least one of Ar and L is an aromatic heterocyclic ring composed of two rings or more and, more preferably, at least one of Ar and L has a fused ring structure represented by general formula (3).

In general formula (1) or (2), Ar or L is represented no less preferably by general formula (4). In this case, if one is an aromatic group represented by general formula (4), the other is an aromatic group having a fused ring structure composed of two rings or more.

In general formula (1) or (2), each of $R_1$ to $R_3$ is independently a hydrogen atom, an alkyl group of 1 to 10 carbon atoms, a cycloalkyl group of 3 to 11 carbon atoms, an aromatic hydrocarbon atom of 6 to 18 carbon atoms, or an aromatic heterocyclic group of 3 to 17 carbon atoms; preferably a hydrogen atom, an alkyl group of 1 to 4 carbon atoms, a cycloalkyl group of 3 to 6 carbon atoms, a phenyl group, a naphthyl group, a pyridyl group, a pyrimidyl group, a triazyl group, or a carbazolyl group; more preferably a hydrogen atom, a phenyl group, or a carbazolyl group. In the case where each of $R_1$ to $R_3$ is a group other than a hydrogen atom, such other group may have a substituent. Examples of a preferable substituent include an alkyl group of 1 to 4 carbon atoms, an alkoxyl group of 1 to 2 carbon atoms, an acetyl group, an aryl group of 6 to 12 carbon atoms, and a heteroaryl group of 3 to 11 carbon atoms. Examples of a more preferable substituent include a phenyl group, a naphthyl group, a carbazolyl group, a quinolyl group, and an isoquinolyl group.

In general formula (1) or (2), n is an integer of 1 to 3, preferably 1 or 2.

When n is 2 or more in general formula (1) or (2), a plurality of Ar's or $R_1$ to $R_3$ may be identical with or different from one another.

In general formula (3), each $X_1$ is independently $CR_4$ or a nitrogen atom, preferably $CR_4$; Y is —O—, —S—, or —$NR_5$—, preferably —S— or —$NR_5$—; Z is a direct bond, —O—, —S—, —$NR_6$—, —$CR_7R_8$—, or a group represented by formula (Z-1), preferably a direct bond, —O—, —S—, or —$NR_6$—, more preferably a direct bond.

Each of the aforementioned $R_4$ to $R_8$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms. At least one of $R_7$ and $R_8$ is preferably a hydrogen atom. When the aromatic group derived from a compound represented by general formula (3) is a monovalent or n-valent aromatic group, one or n number of $R_4$ to $R_8$ come off to be replaced by a direct bond. One of the direct bonds is linked to the 1 or 9 position of the central carbazole ring. In the case where L has two direct bonds or more, one is linked to the central carbazole ring while the others are linked to other carbazole rings.

Each of $R_4$ to $R_8$ is preferably a hydrogen atom, an alkyl group of 1 to 4 carbon atoms, a cycloalkyl group of 3 to 6 carbon atoms, a phenyl group, a naphthyl group, a pyridyl group, a pyrimidyl group, a triazyl group, or a carbazolyl group, more preferably, a hydrogen atom, a phenyl group, or a carbazolyl group. In the case where each of $R_4$ to $R_8$ is a group other than a hydrogen atom, such other group may have a substituent. Examples of a preferable substituent include an alkyl group of 1 to 4 carbon atoms, an alkoxyl group of 1 to 2 carbon atoms, an acetyl group, an aryl group of 6 to 12 carbon atoms, and a heteroaryl group of 3 to 11 carbon atoms. Examples of a more preferable substituent include a phenyl group, a naphthyl group, a carbazolyl group, a quinolyl group, and an isoquinolyl group.

In general formula (4), each $X_2$ is independently $CR_9$ or a nitrogen atom, preferably $CR_9$.

In general formula (4), each of $R_9$ to $R_{12}$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms. When a compound represented by general formula (4) generates a monovalent or n-valent aromatic group, one or n number of $R_9$ to $R_{12}$ come off to be replaced by a direct bond. One of the direct bonds is linked to the 1 or 9 position of the central carbazole ring. In the case where L has two direct bonds or more, one is linked to the central carbazole ring while the others are linked to other carbazole rings.

Each of $R_9$ to $R_{12}$ is preferably a hydrogen atom, an alkyl group of 1 to 4 carbon atoms, a cycloalkyl group of 3 to 6 carbon atoms, a phenyl group, a naphthyl group, a pyridyl group, a pyrimidyl group, a triazyl group, or a carbazolyl group, more preferably, a hydrogen atom, a phenyl group, or a carbazolyl group. In the case where each of $R_9$ to $R_{12}$ is a group other than a hydrogen atom, such other group may have a substituent. Examples of a preferable substituent include an alkyl group of 1 to 4 carbon atoms, an alkoxyl group of 1 to 2 carbon atoms, an acetyl group, an aryl group of 6 to 12 carbon atoms, and a heteroaryl group of 3 to 11 carbon atoms. Examples of a more preferable substituent include a phenyl group, a naphthyl group, a carbazolyl group, a quinolyl group, and an isoquinolyl group.

In general formula (1) or (2), the T1 energy is 2.85 eV or more, preferably 2.90 eV or more, more preferably 3.00 eV or more.

The values of the T1 energy as used in this specification are values obtained using Gaussian 03, a software for molecular calculation manufactured by Gaussian Inc. of USA and are defined as values obtained by structure optimization calculation at the B3LYP/6-31G*B3LYP/cc-pVDZ level.

The 1,9-substituted carbazole compound to be used in this invention can be synthesized by a known method by using a carbazole derivative having a halogen atom as a substituent at the 1 position as a starting material and selecting raw materials according to the structure of the target compound.

For example, the 1-fluorocarbazole skeleton of a carbazole derivative having a fluorine atom as a substituent at the 1 position can be synthesized by the following reaction with reference to a synthetic example described in Angew. Chem., Int. Ed., 2007, No. 46, pp 1627-1629.

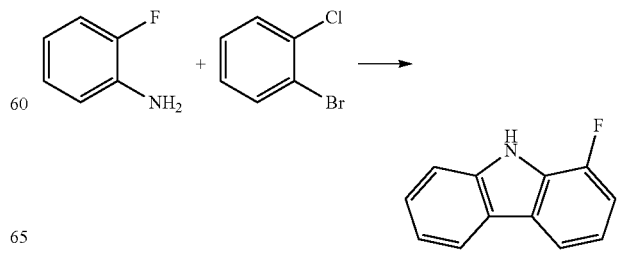

On the other hand, the 1-bromocarbazole skeleton of a carbazole derivative having a bromine atom as a substituent at the 1 position can be synthesized by the following reaction with reference to synthetic examples described in Synlett, 2000, No. 30, pp 131-140 and J. Org. Chem., No. 66, pp 8612-8615.

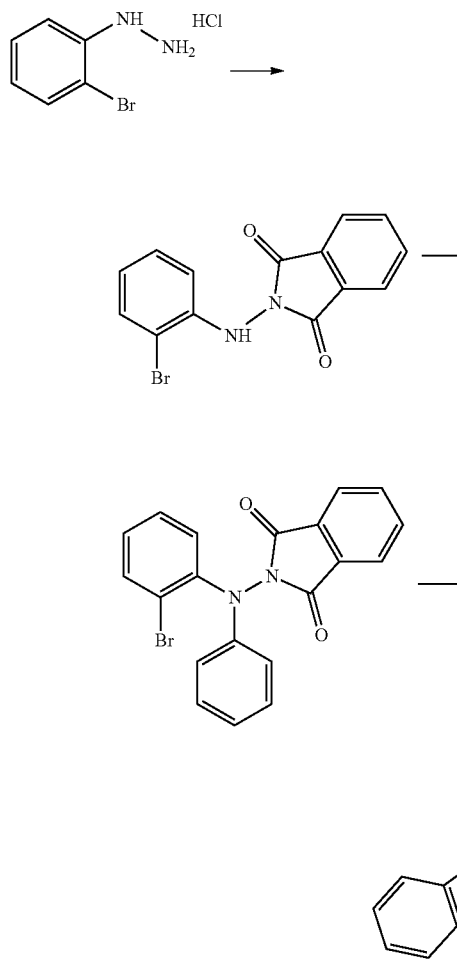

Specific examples of the 1,9-substituted carbazole compounds represented by general formulas (1) and (2) are illustrated below, but the 1,9-substituted carbazole compounds to be used in this invention are not limited thereto.

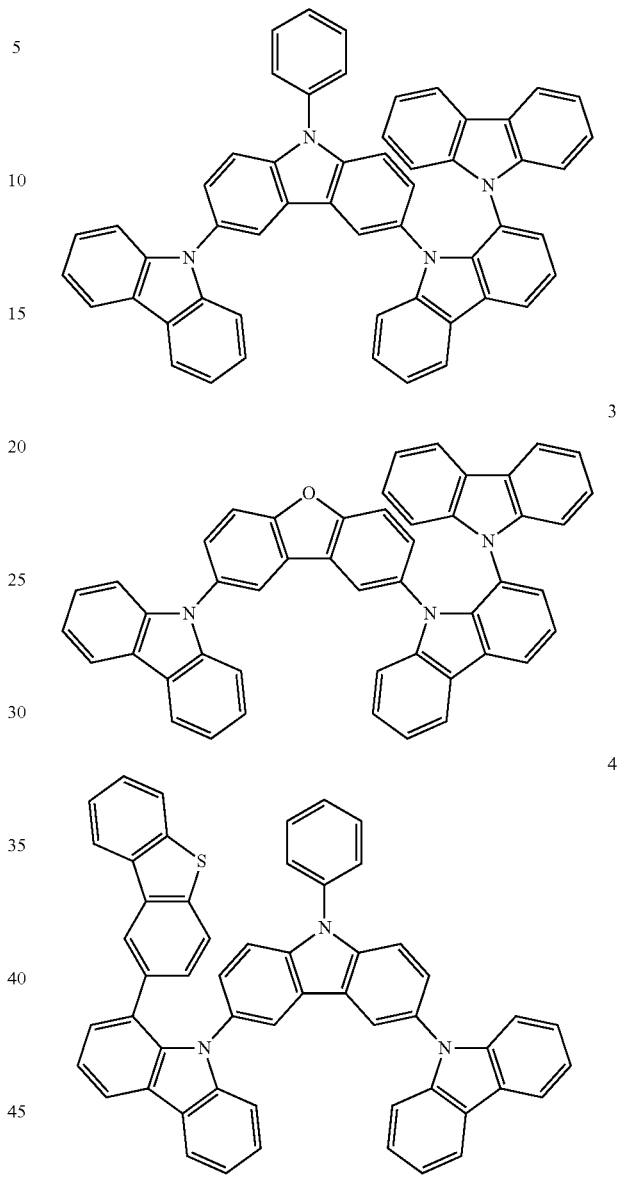

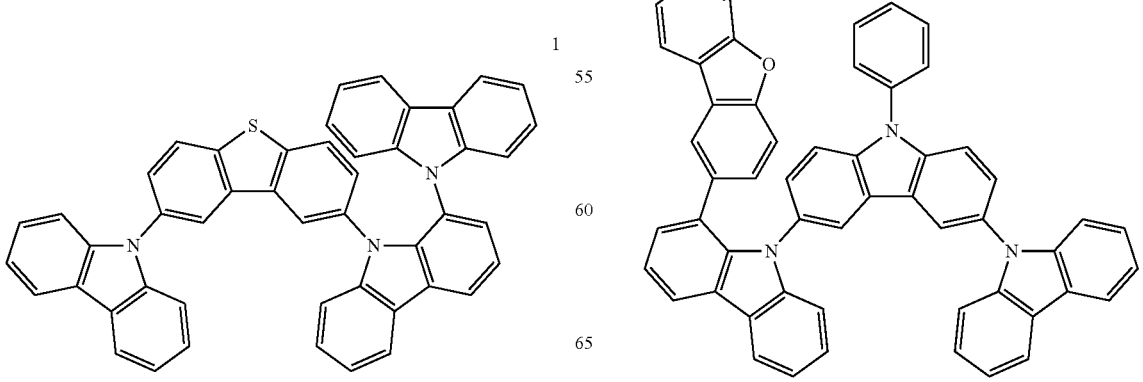

-continued
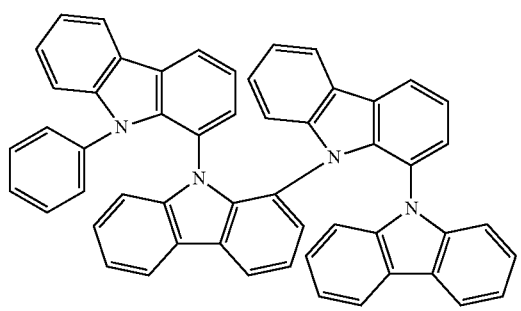
6
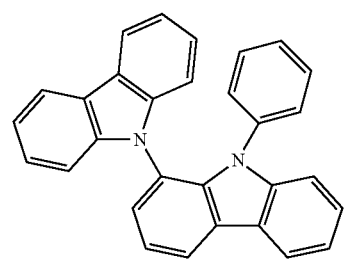
7
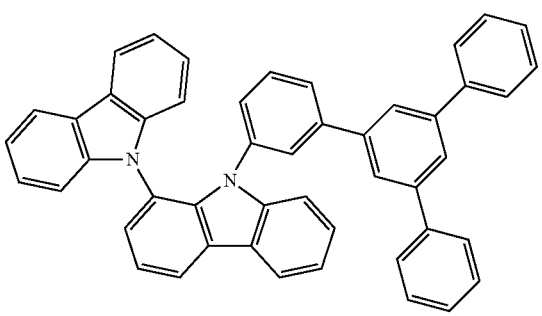
8
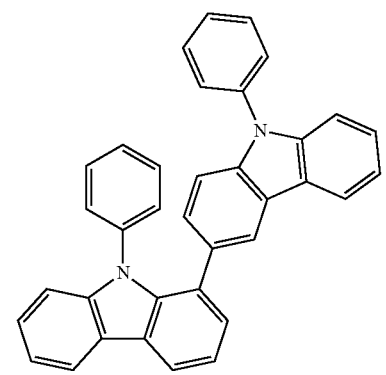
9
-continued
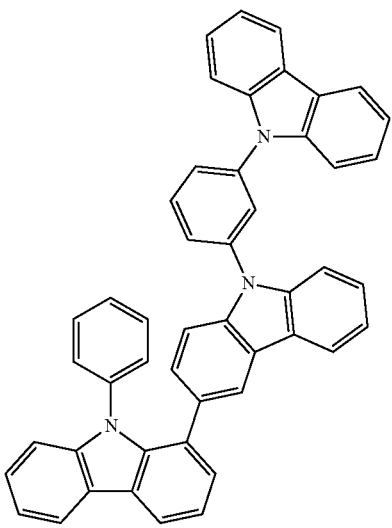
10
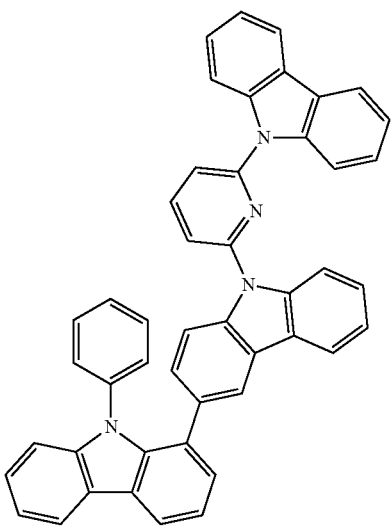
11
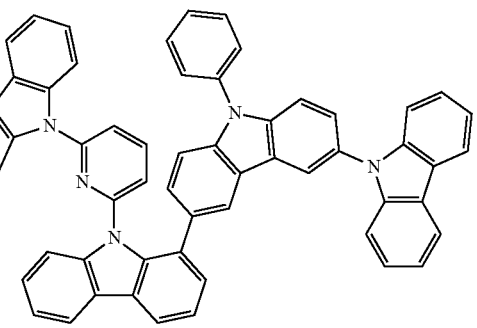
12

13
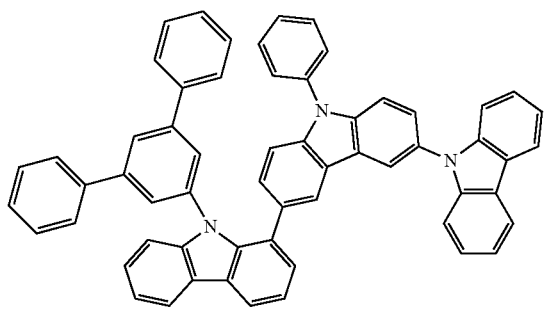
14
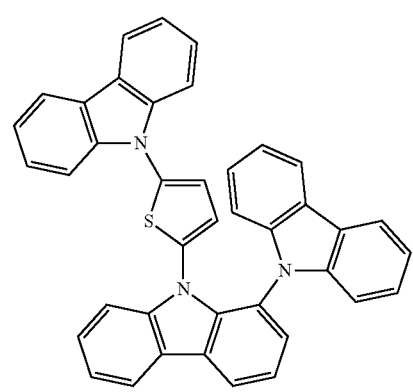
15
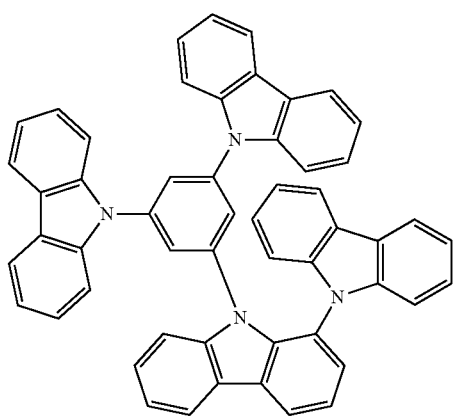
16
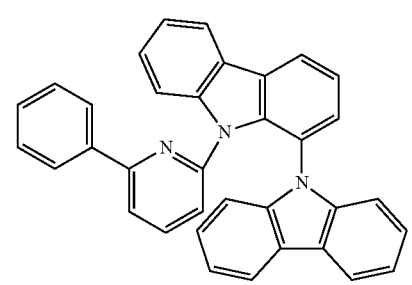
17
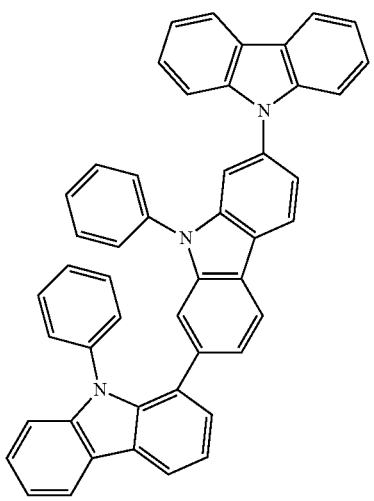
18
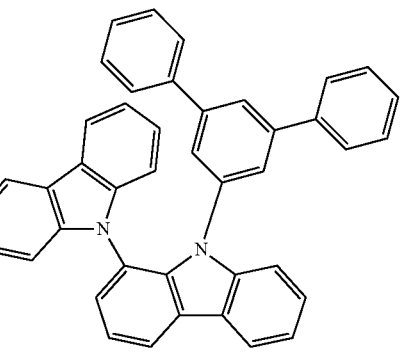
19
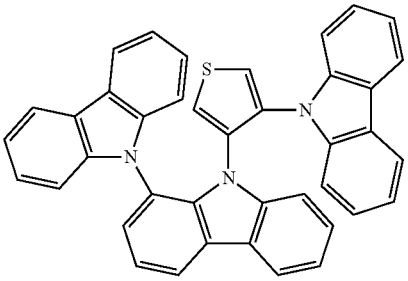
20
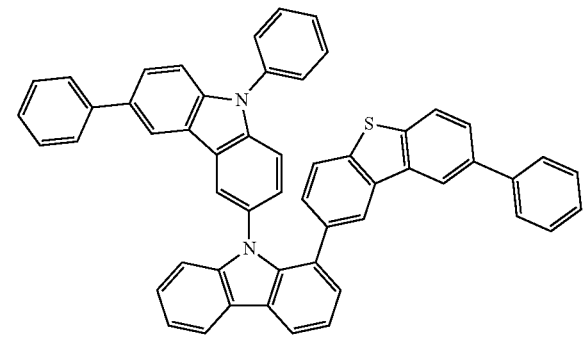

21
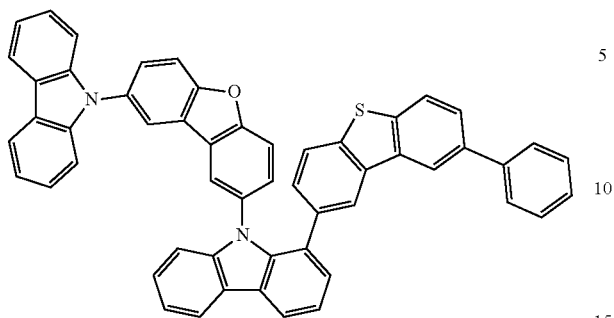
22
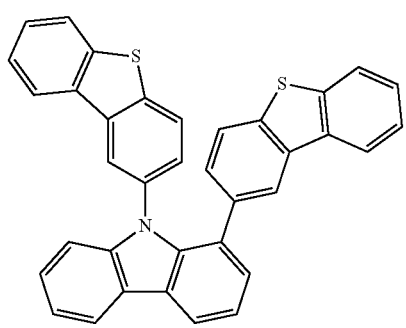
23
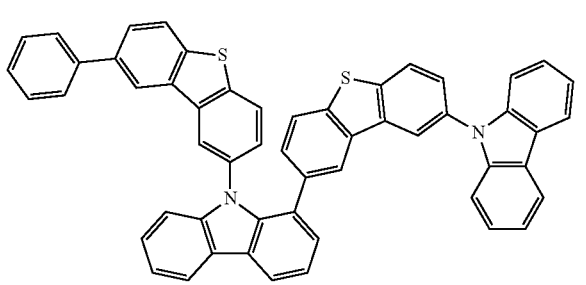
24
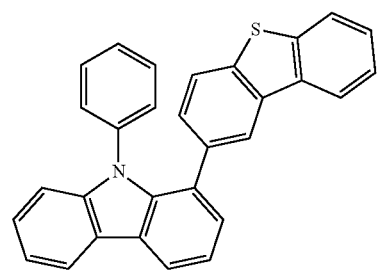
25
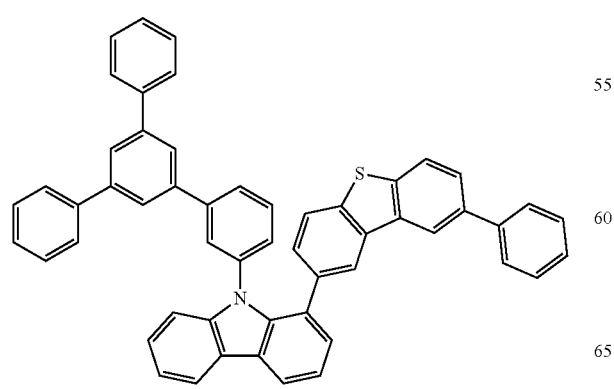
26
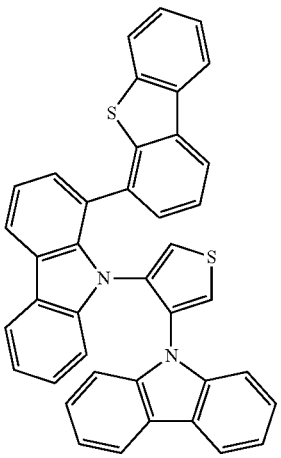
27
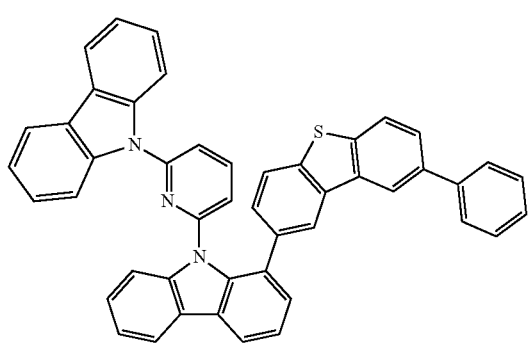
28
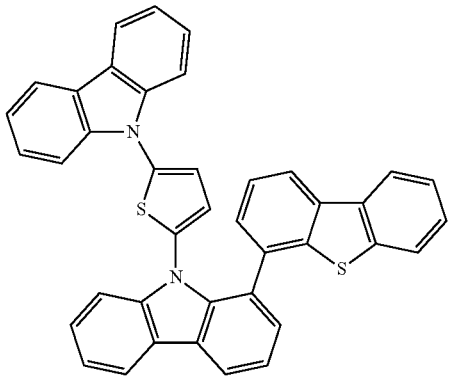
29
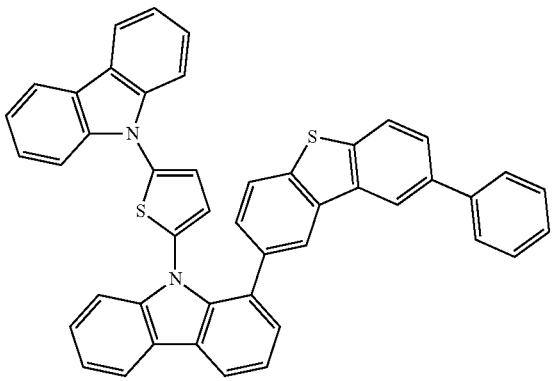

30
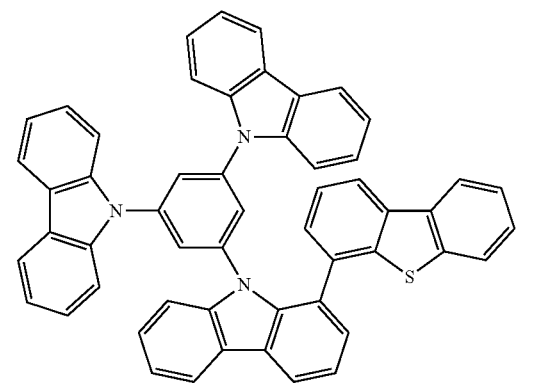
31
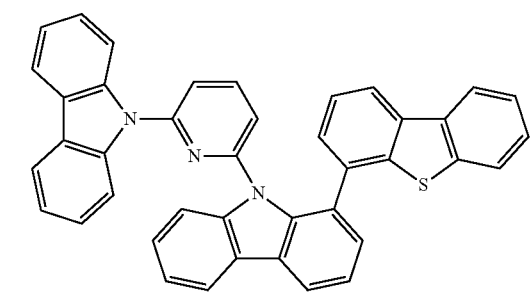
32
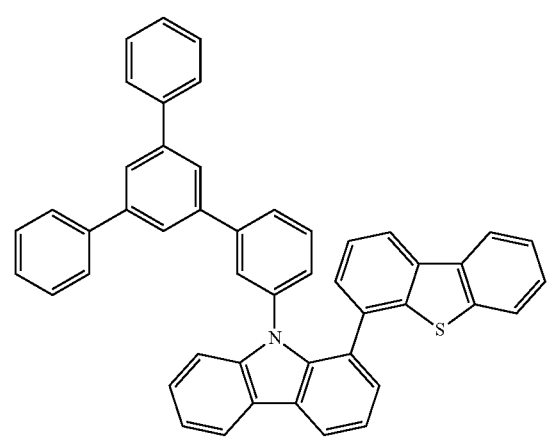
33
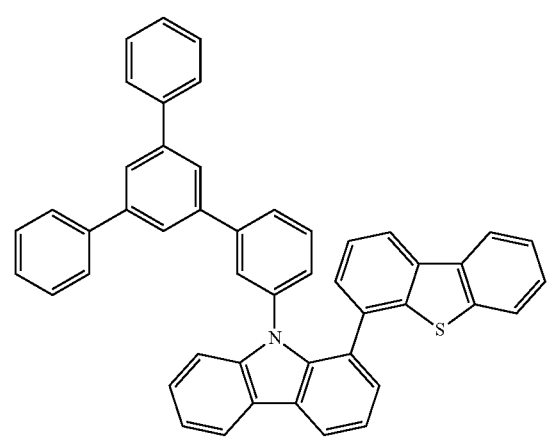
34
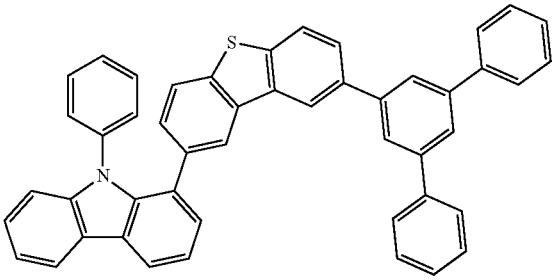
35
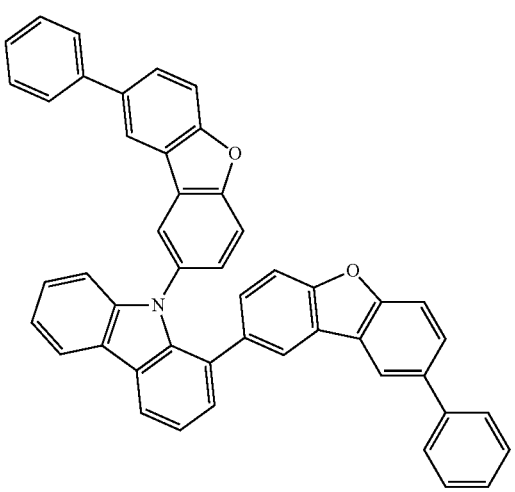
36
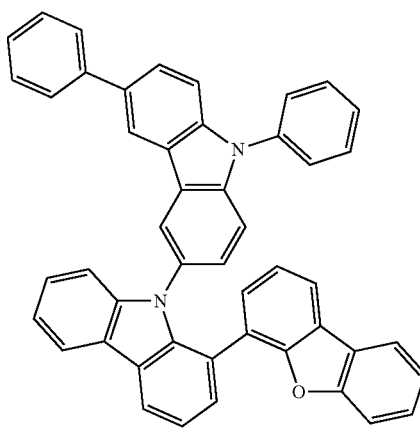
37
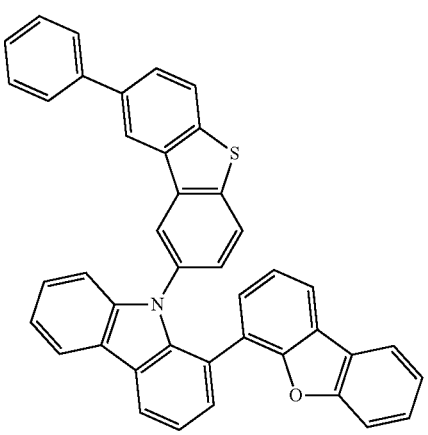

38
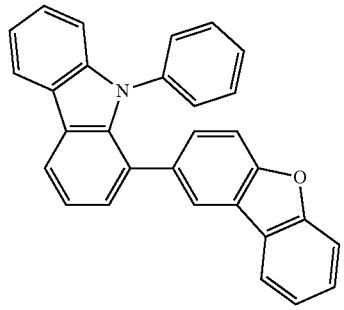
39
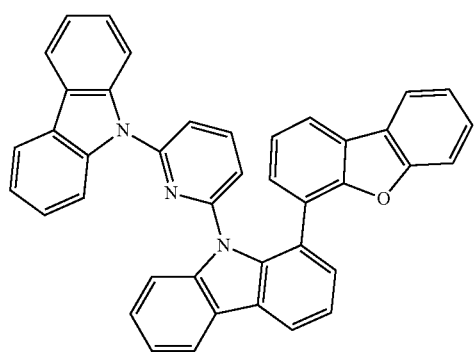
40
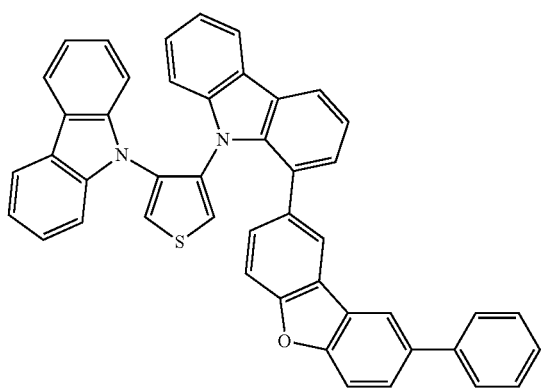
41
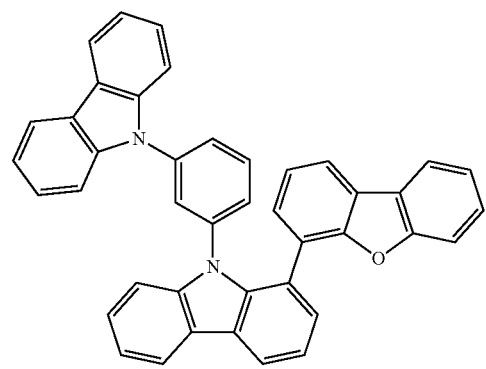
42
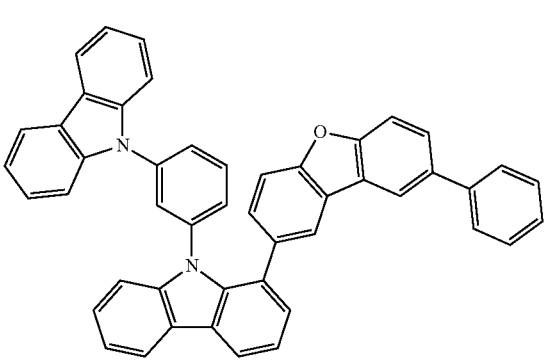
43
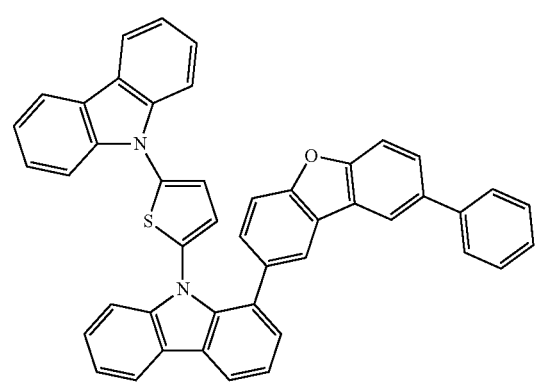
44
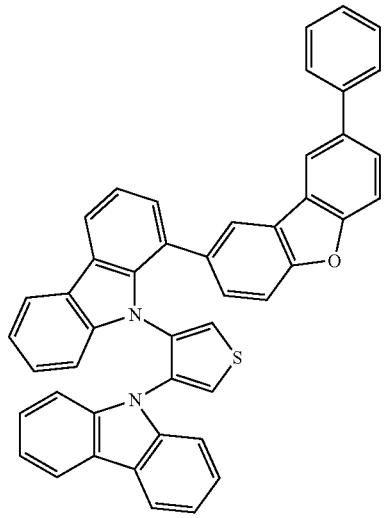
45
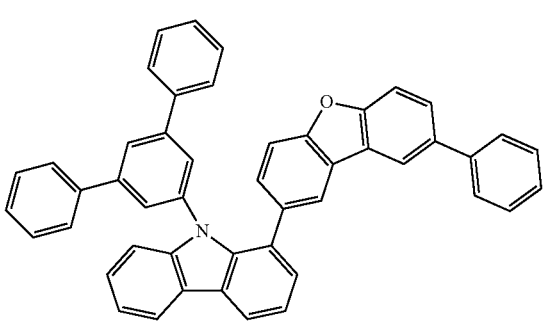

46
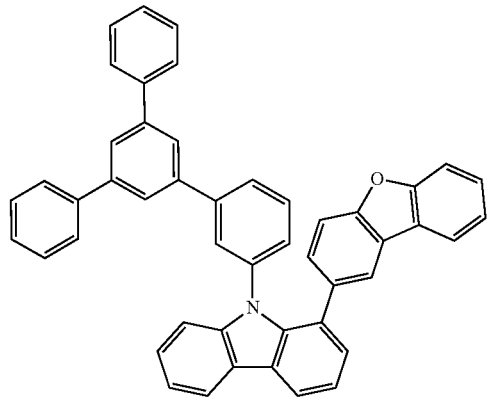
47
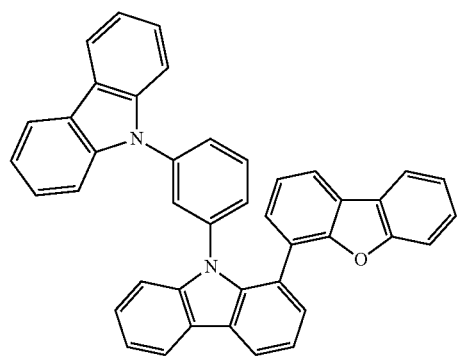
48
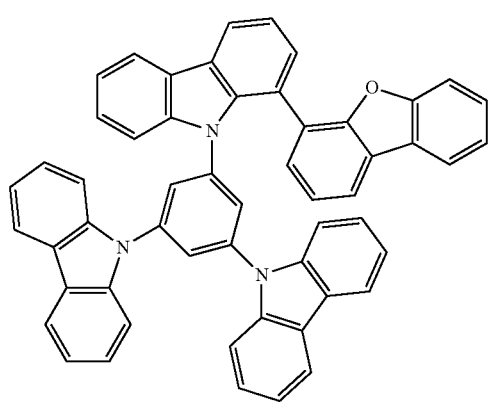
49
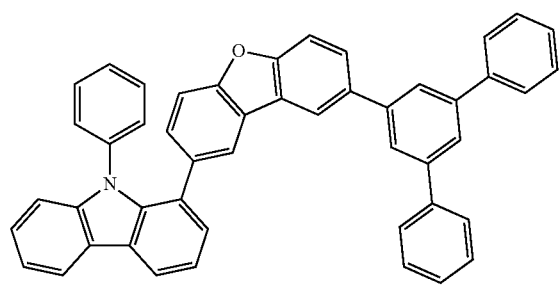
50
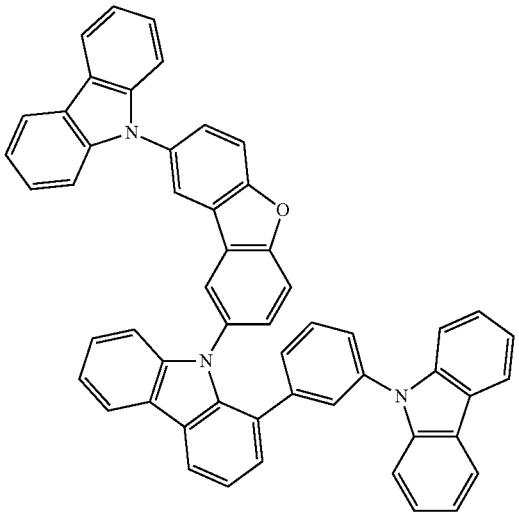
51
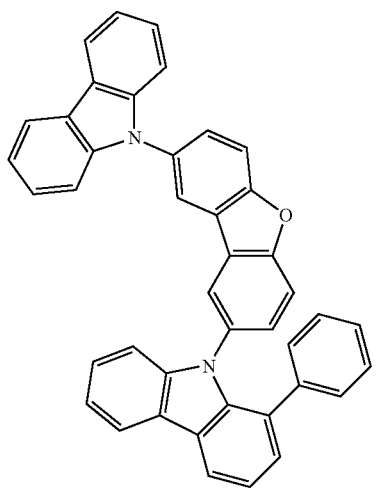
52
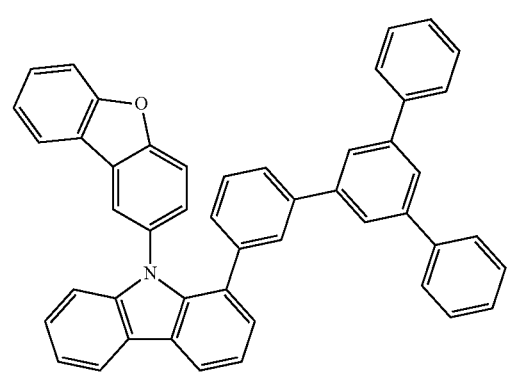

-continued
53
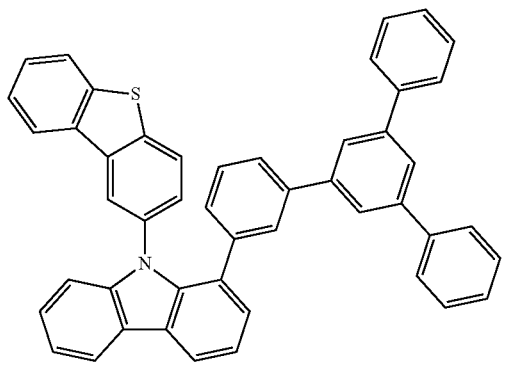
54
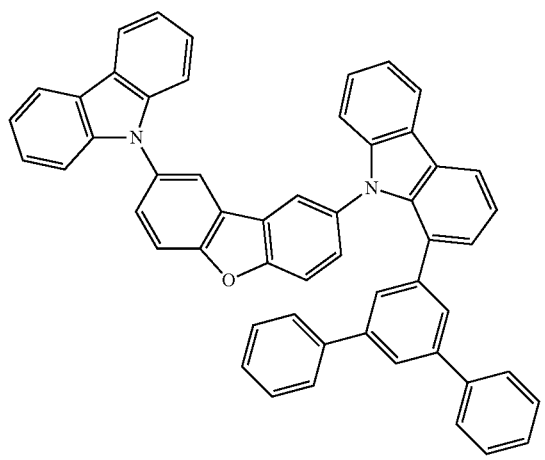
55
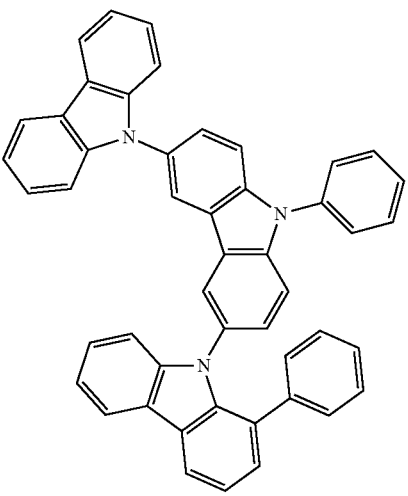
56
57
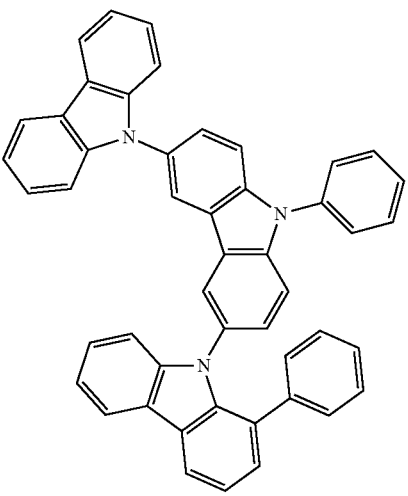
58
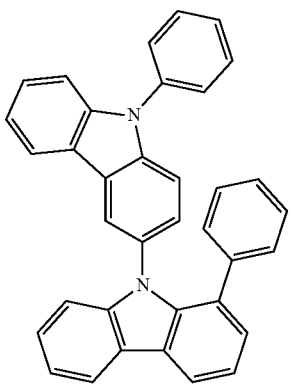
59
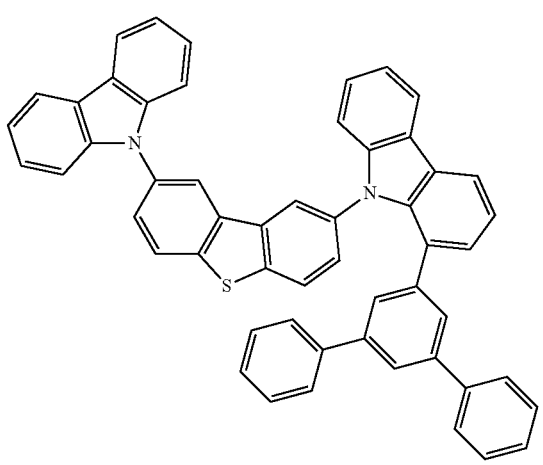

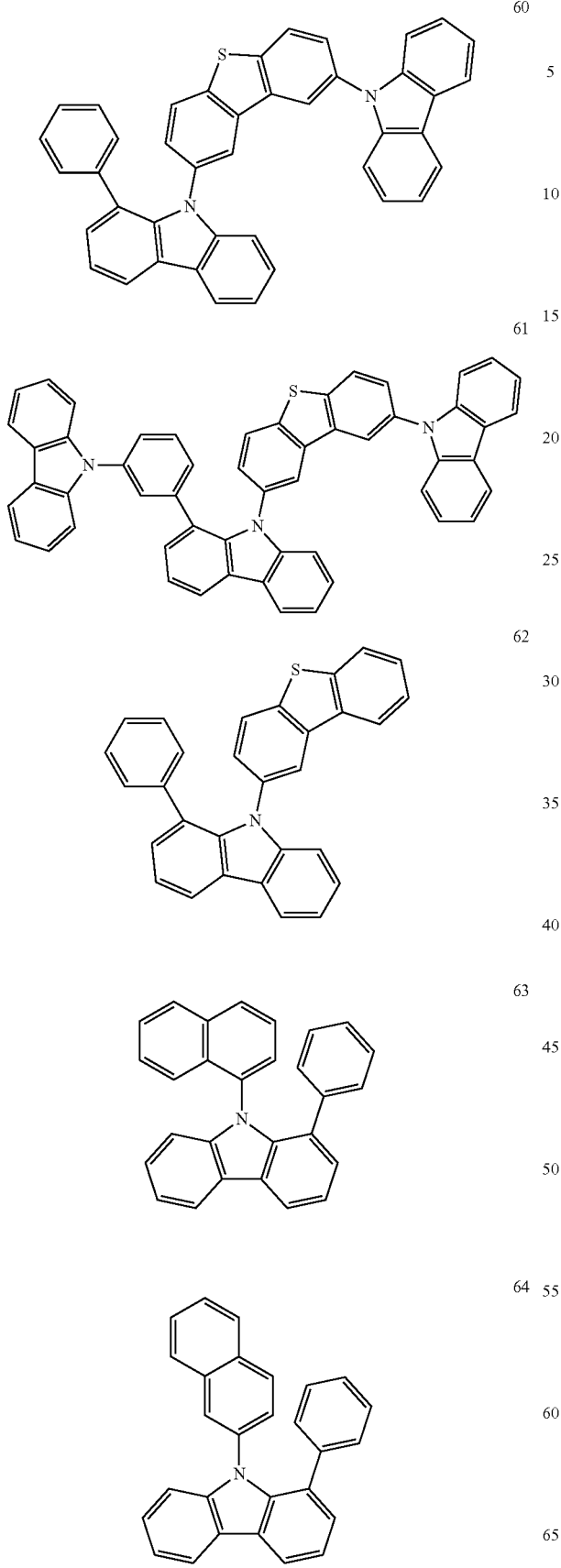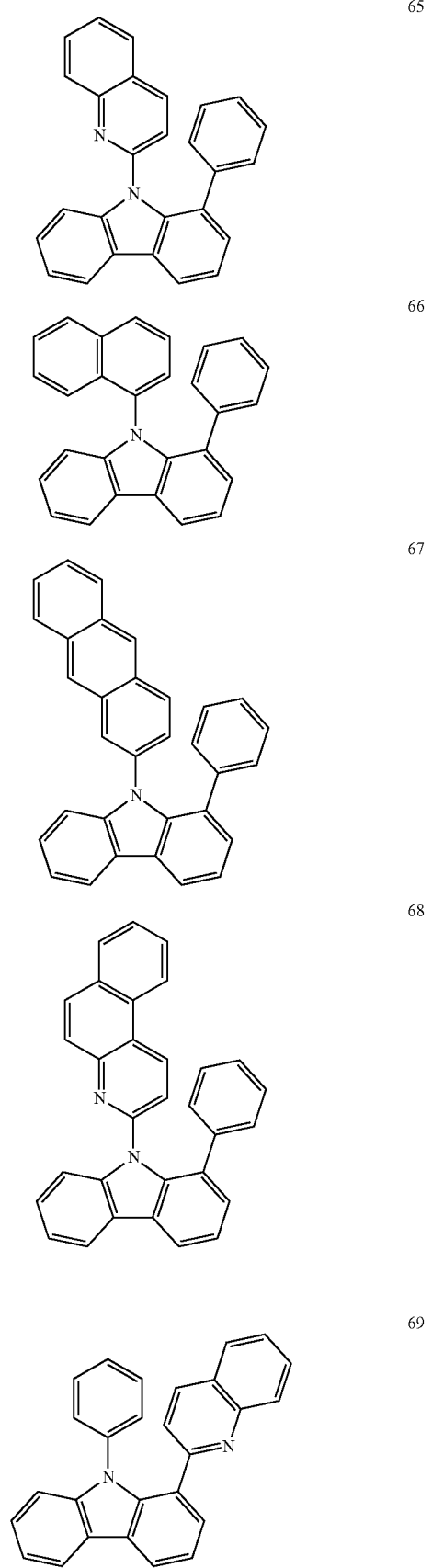

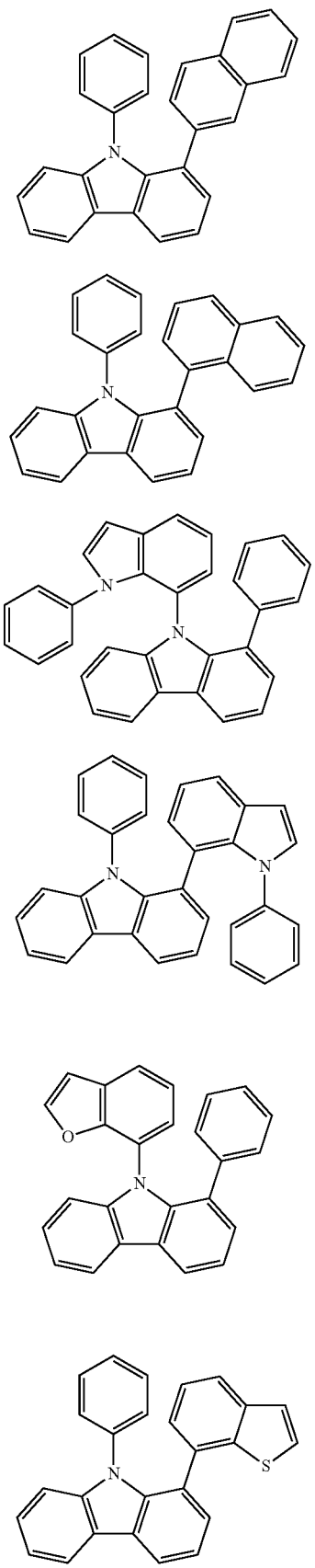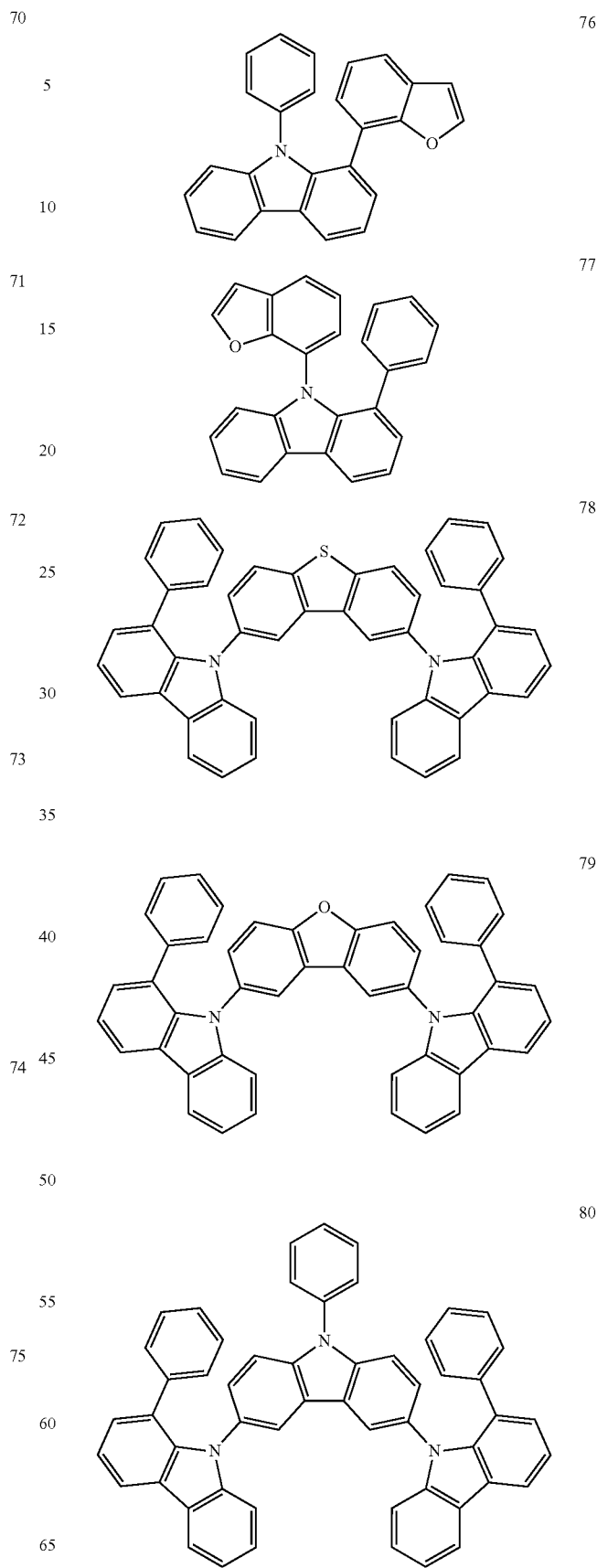

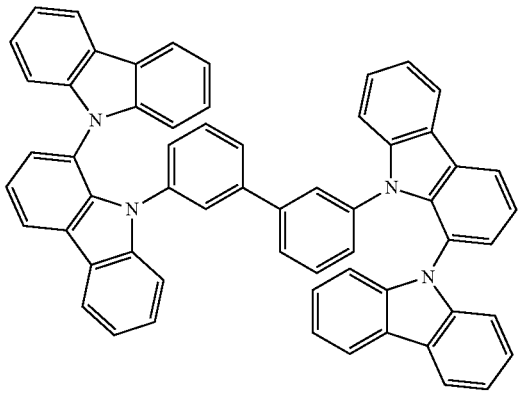
81
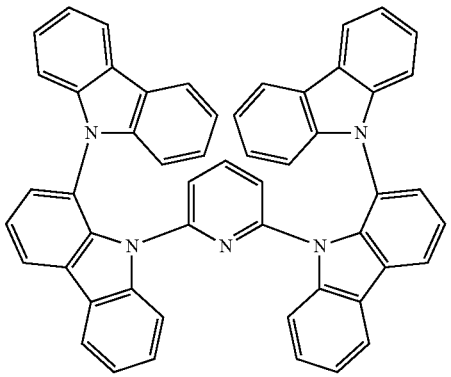
85
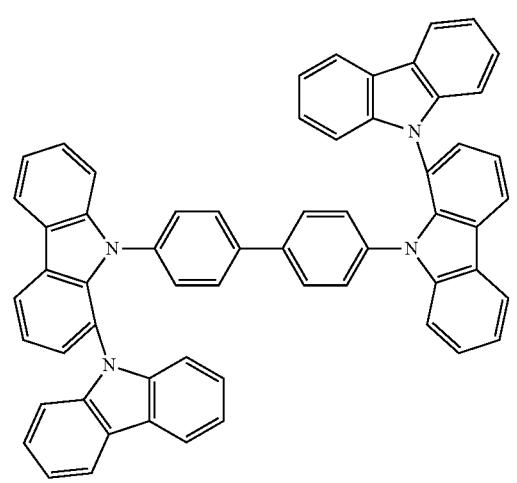
82
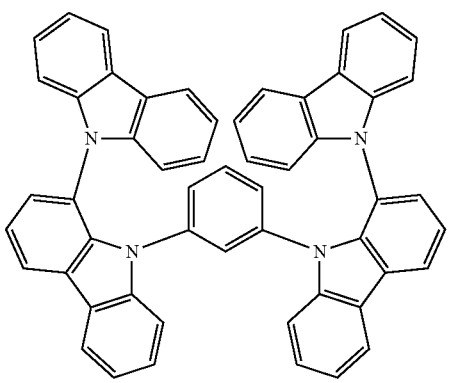
86
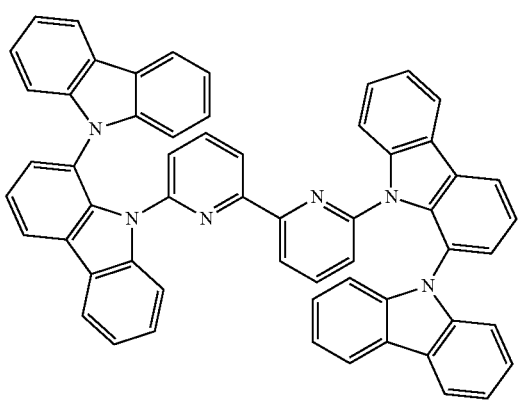
83
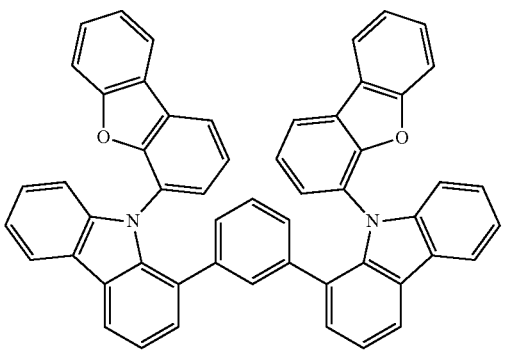
87
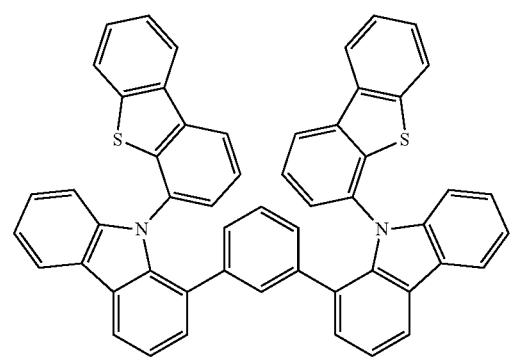
84
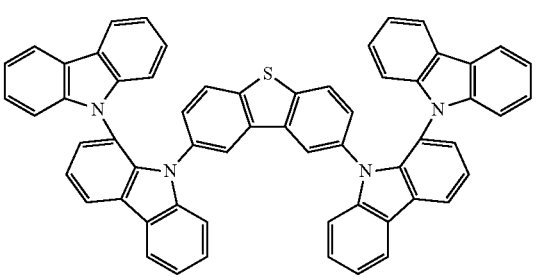
88

89
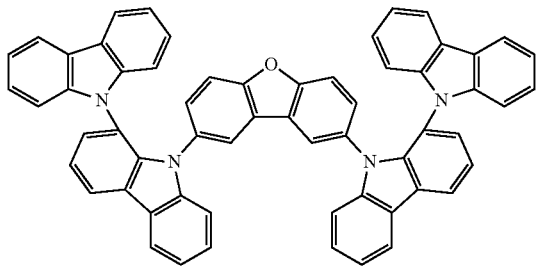
90
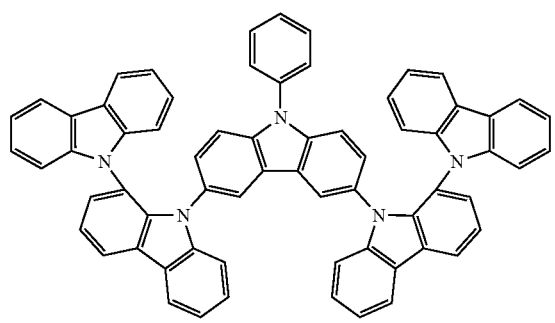
91
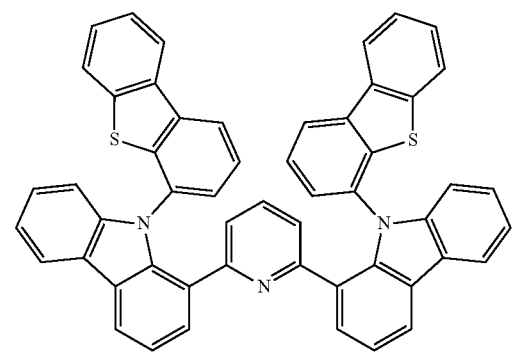
92
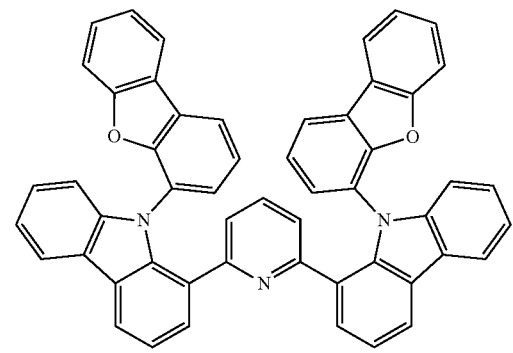
93
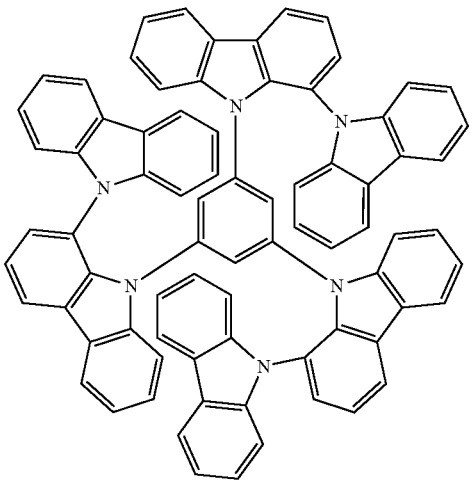
94
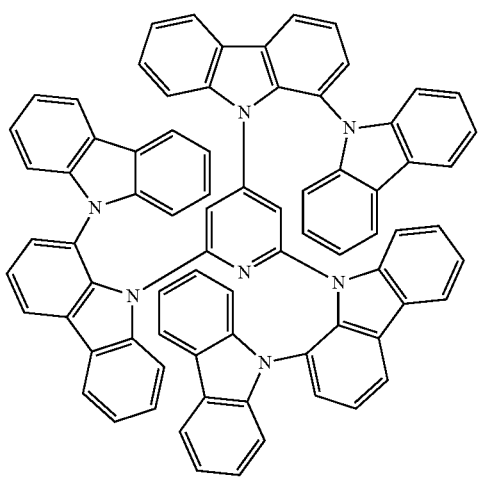
95
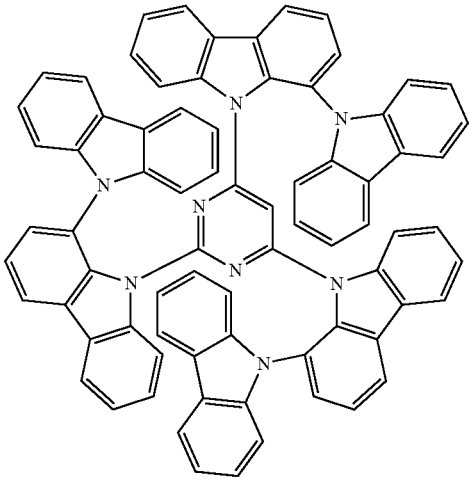

96
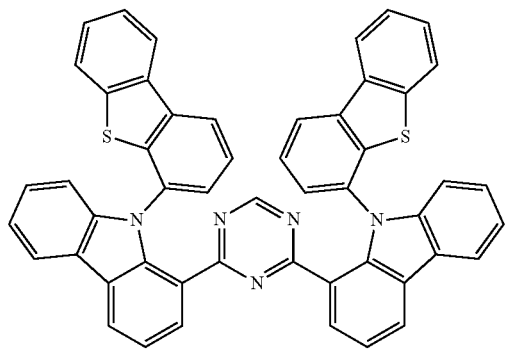
97
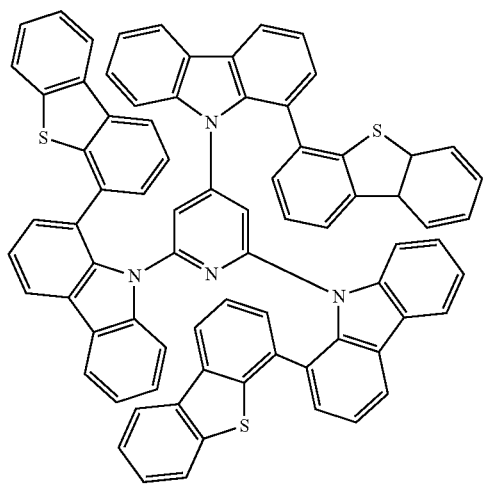
98
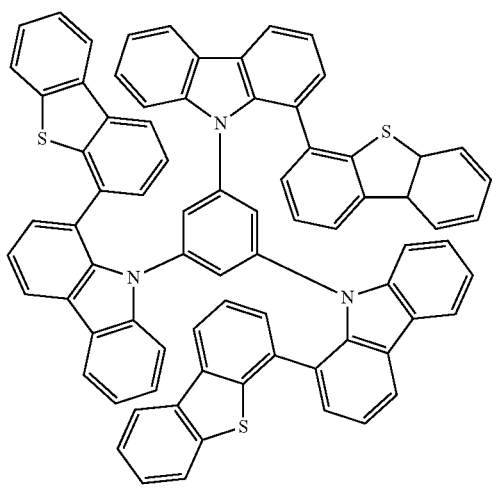
99
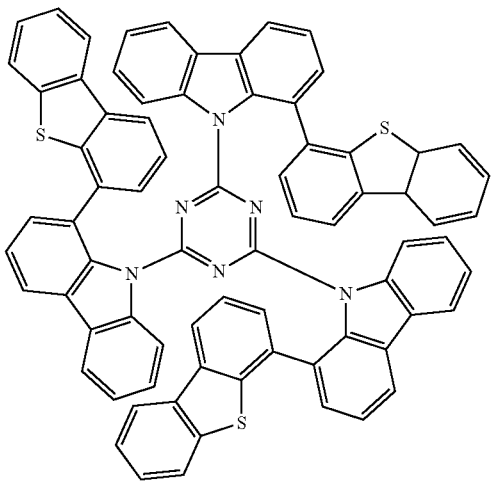
100
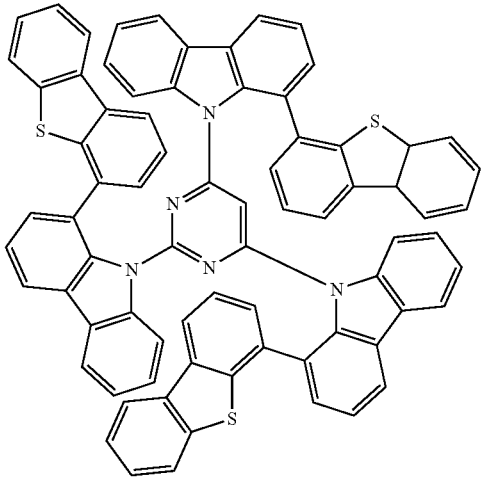
101
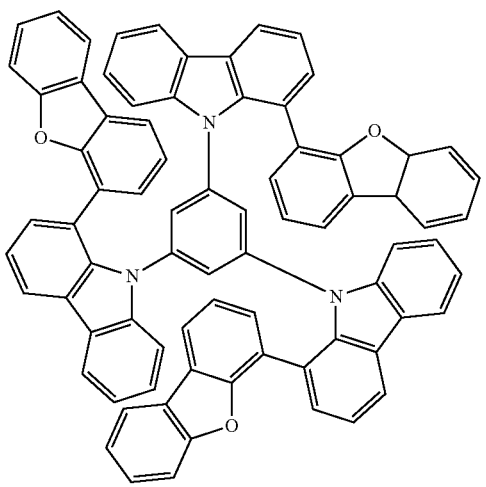

-continued

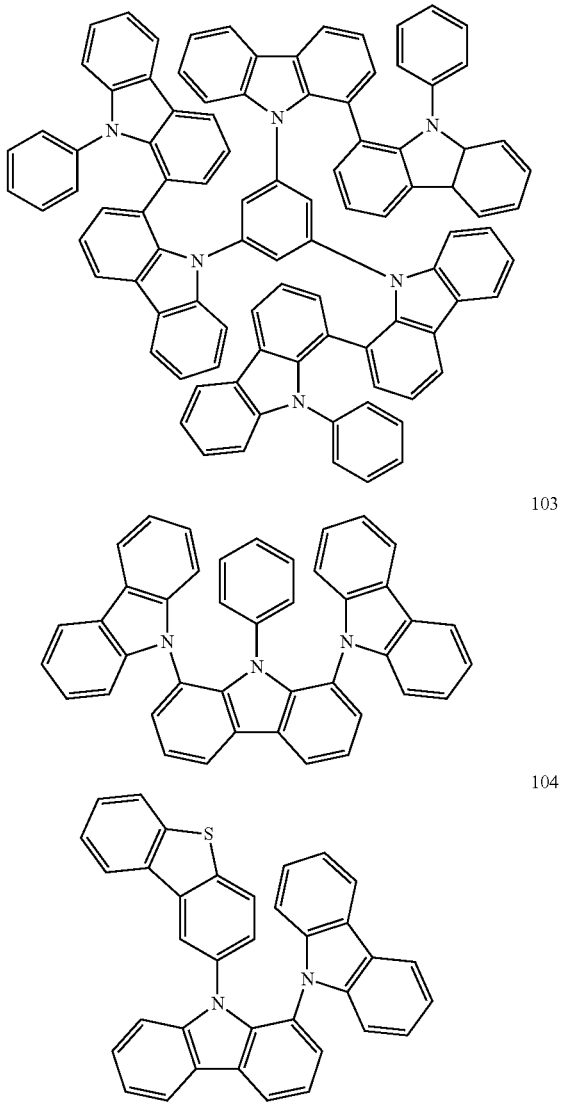

Provided that an organic EL device comprises an anode, a plurality of organic layers, and a cathode piled one upon another on a substrate, incorporation of the 1,9-substituted carbazole compound of this invention in at least one of the organic layers helps to provide an excellent organic EL device. An organic layer suitable for this purpose is a light-emitting layer, a hole-transporting layer, an electron-transporting layer, or a hole-blocking layer. Preferably, the 1,9-substituted carbazole compound is incorporated as a host material in a light-emitting layer containing a phosphorescent dopant.

An organic EL device according to this invention is explained hereinafter.

The organic EL device of this invention comprises at least one organic layer comprising a light-emitting layer and, further, at least one organic layer containing a 1,9-substituted carbazole compound between an anode and a cathode piled one upon another on a substrate. Advantageously, the 1,9-substituted carbazole compound is contained in a light-emitting layer together with a phosphorescent dopant.

The structure of the organic EL device of this invention is explained hereinafter with reference to the drawing, but it will not be limited to the one illustrated in the drawing.

FIG. 1 schematically illustrates an example of the structure of an organic EL device generally used in this invention and the numbers in FIG. 1 stand for the following: 1 for a substrate, 2 for an anode, 3 for a hole-injecting layer, 4 for a hole-transporting layer, 5 for a light-emitting layer, 6 for an electron-transporting layer, and 7 for a cathode. The organic EL device of this invention may further comprise an exciton-blocking layer adjacent to the light-emitting layer or an electron-blocking layer between the light-emitting layer and the hole-injecting layer. The exciton-blocking layer may be inserted either on the anode side or on the cathode side of the light-emitting layer or may be inserted simultaneously on both sides. The organic EL device of this invention comprises the substrate, the anode, the light-emitting layer, and the cathode as essential layers. However, it is preferable that the device comprises a hole-injecting/transporting layer and an electron-injecting/transporting layer in addition to the essential layers and further comprises a hole-blocking layer between the light-emitting layer and the electron-injecting/transporting layer. The hole-injecting/transporting layer means a hole-injecting layer and/or a hole-transporting layer while the electron-injecting/transporting layer means an electron-injecting layer and/or an electron-transporting layer.

The organic EL device of this invention can be so constructed as to have a structure that is the reverse of the structure illustrated in FIG. 1 by piling the cathode 7, the electron-transporting layer 6, the light-emitting layer 5, the hole-transporting layer 4, and the anode 2 one upon another in this order on the substrate 1. In this case, it is possible to add or omit a layer or layers according to the need.

—Substrate—

The organic EL device of this invention is preferably supported by a substrate. There is no specific restriction on the substrate and any of the substrates which have been used customarily in organic EL devices can be used. A substrate made from a material such as glass, transparent plastic, and quartz may be used.

—Anode—

The anode of an organic EL device is preferably made from an electrode substance having a high work function (4 eV or more) such as a metal, an alloy, an electrically conductive compound, and a mixture thereof. Specific examples of the electrode substances of this kind include metals such as Au and electrically conductive transparent materials such as CuI, indium tin oxide (ITO), $SnO_2$, and ZnO. Further, a material such as IDIXO ($In_2O_3$—ZnO) which is amorphous and formable into a transparent electrically conductive film may be used. The anode may be formed by preparing a thin film from any of those electrode substances by a method such as vapor deposition and sputtering and then forming a pattern of desired shape on the thin film by photolithography. Or, in the case where high accuracy is not required in patterning (100 μm or more), a pattern may be formed through a mask of desired shape during vapor deposition or sputtering of the aforementioned electrode substance. In the case where a substance which is applicable by a coating method such as an electrically conductive organic compound is used, a wet film-forming process such as printing and coating may be employed. When emitted light is taken out from the anode, the transmittance is desirably set at 10% or more and the sheet resistance as the anode is preferably several hundred Ω/□ or less. Further, the thickness of the film is normally selected from the range of 10 to 1,000 nm, preferably 10 to 200 nm, although it varies with the film-forming material.

—Cathode—

Meanwhile, the cathode is made from an electrode substance having a low work function (4 eV or less) such as a metal, an alloy, an electrically conductive compound, and a mixture thereof. Specific examples of the electrode substances of this kind include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. From the viewpoint of electron-injecting property and durability against oxidation and the like, a mixture of an electron-injecting metal and a second metal which is higher in work function and more stable than the electron-injecting metal is suitable for use as an electrode substance and examples thereof include a magnesium/silver mixture, a magnesium/aluminum mixture, a magnesium/indium mixture, an aluminum/aluminum oxide ($Al_2O_3$) mixture, a lithium/aluminum mixture, and aluminum. The cathode is formed by preparing a thin film from any of those electrode substances by a method such as vapor deposition and sputtering. The sheet resistance as the cathode is preferably several hundred Ω/□ or less and the thickness of the film is selected from the range of 10 nm to 5 μm, preferably 50 to 200 nm. Making either the anode or the cathode of an organic EL device transparent or translucent in order to transmit emitted light advantageously improves the luminance.

A transparent or translucent cathode may be made by forming a cathode with a film thickness of 1 to 20 nm from the aforementioned metal and then forming thereon a film of one of the electrically conductive transparent materials described above in explanation of the anode. This method can be applied to fabricate a device in which both the anode and the cathode display good transmittance properties.

—Light-Emitting Layer—

The light-emitting layer is a phosphorescent light-emitting layer and contains a phosphorescent dopant and a host material. Examples of the phosphorescent dopant include an organic metal complex containing at least one metal selected from ruthenium, rhodium, palladium, silver, rhenium, osmium, iridium, platinum, and gold. The organic metal complexes of this kind are known in the aforementioned prior art technical documents and elsewhere and a suitable organic metal complex may be selected from them and used. It is preferable that light emitted from the phosphorescent dopant has a peak wavelength below 550 nm.

Preferable examples of the phosphorescent dopant include a complex containing a noble metal element such as Ir in the center, typically Ir(ppy)$_3$, a complex such as (Bt)$_2$Iracac, and a complex such as (Btp)Ptacac. Specific examples of those complexes are illustrated below, but the complexes useful for this invention are not limited thereto.

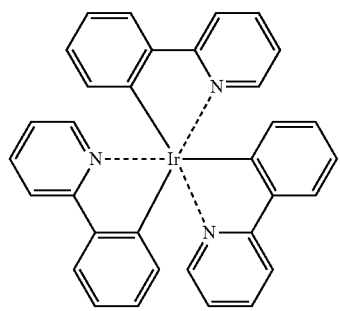

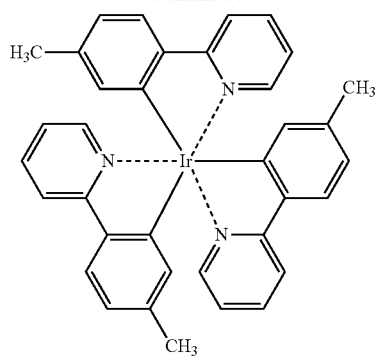

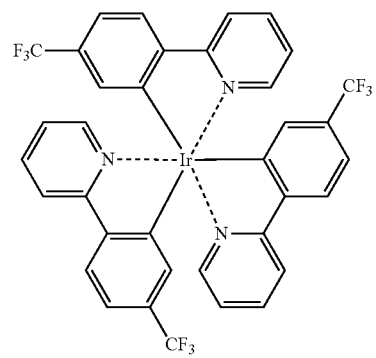

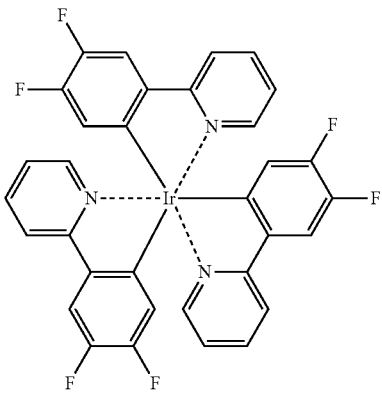

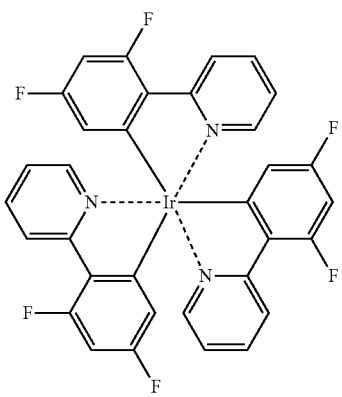

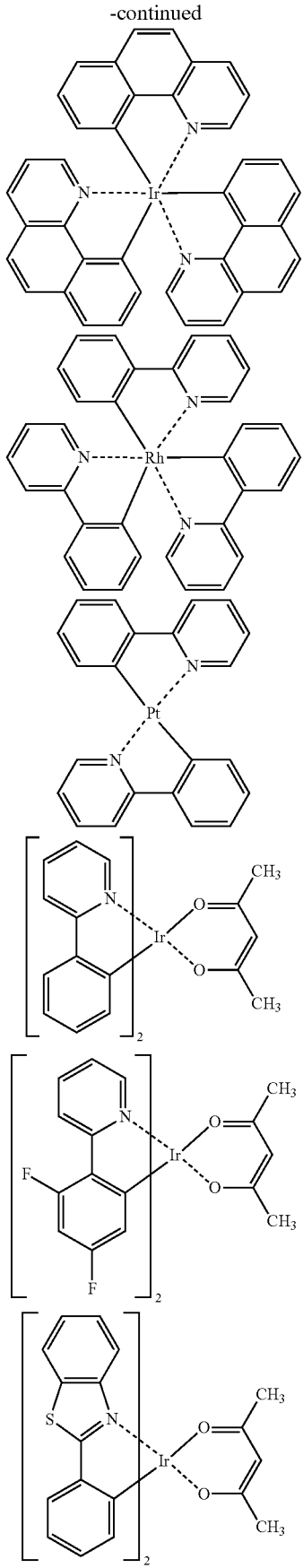
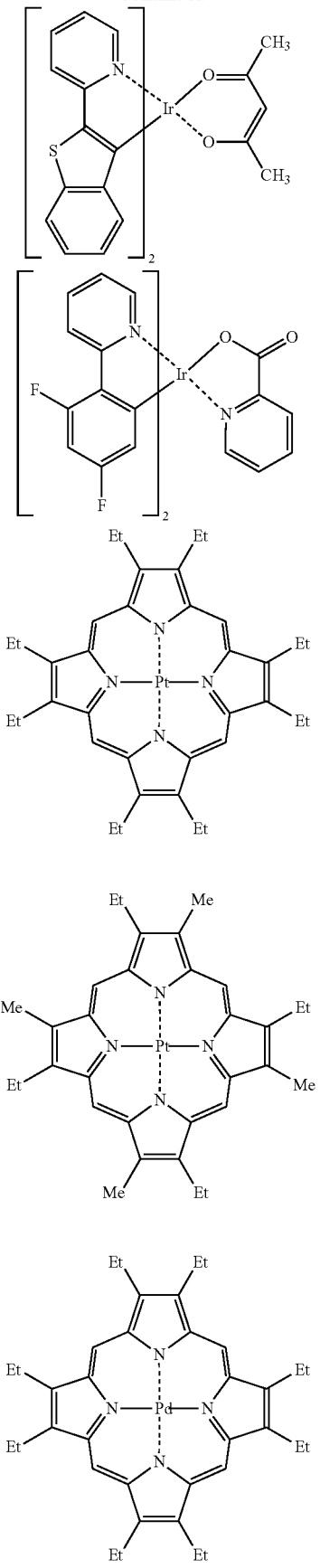

-continued

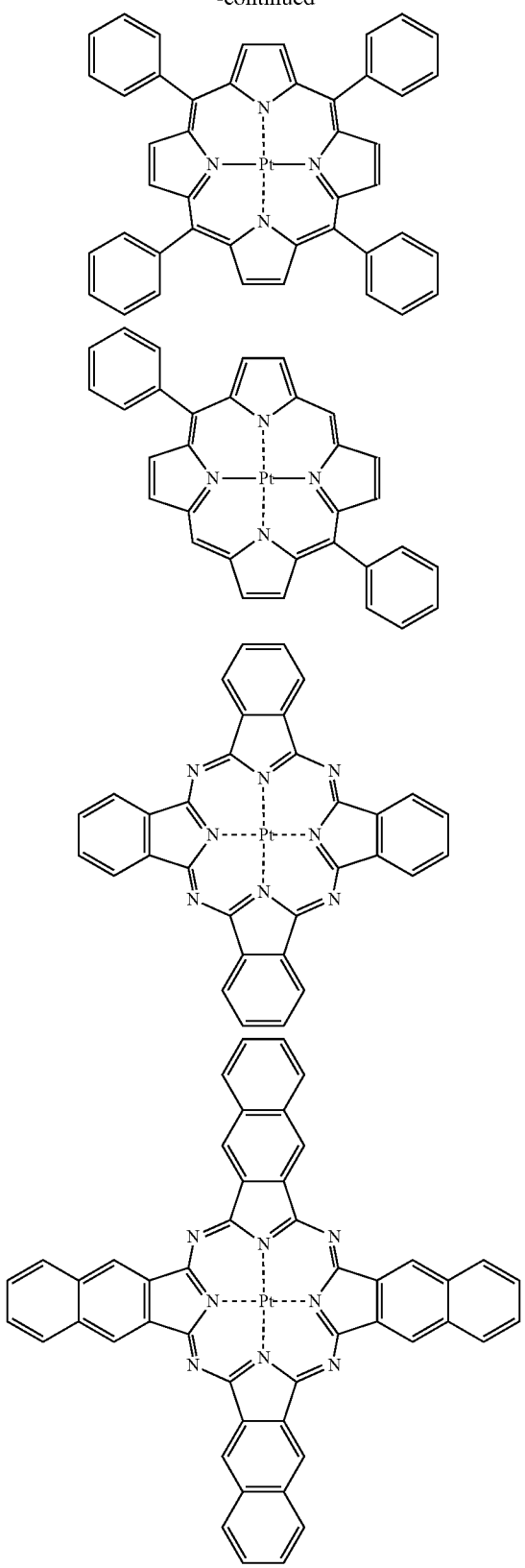

The content of the aforementioned phosphorescent dopant in the light-emitting layer is preferably in the range of 5 to 30 wt %.

It is preferable to use a 1,9-substituted carbazole compound as a host material in the light-emitting layer. However, in the case where the said carbazole compound is used in an organic layer other than the light-emitting layer, a host material other than the 1,9-substituted carbazole compound may be used in the light-emitting layer. Further, the 1,9-substituted carbazole compound may be used together with other host material. Still further, plural kinds of known host materials may be used together.

Among the known host compounds, those which are suitable for use preferably have abilities to transport holes and electrons, can prevent the wavelength of emitted light from shifting to longer wavelengths, and have a high glass transition temperature.

Such host materials other than the 1,9-substituted carbazole compounds are known in a large number of patent documents and elsewhere and a suitable material may be selected from them. Specific examples include, but are not limited to, indole derivatives, carbazole derivatives, indolocarbazole derivatives, triazole derivatives, oxazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, styrylanthracene derivatives, fluorenone derivatives, hydrazone derivatives, stilbene derivatives, silazane derivatives, aromatic tertiary amine compounds, styrylamine compounds, aromatic dimethylidene-based compounds, porphyrin-based compounds, anthraquinodimethan derivatives, anthrone derivatives, diphenylquinone derivatives, thiopyran dioxide derivatives, heterocyclic tetracarboxylic acid anhydrides of naphthalene and perylene, a variety of metal complexes represented by metal complexes of phthalocyanine derivatives and 8-quinolinol derivatives, metal phthalocyanines, and metal complexes of benzoxazole derivatives and benzothiazole derivatives, and polymer compounds such as polysilane-based compounds, poly(N-vinylcarbazole) derivatives, aniline-based copolymers, thiophene oligomers, polythiophene derivatives, polyphenylene derivatives, polyphenylenevinylene derivatives, and polyfluorene derivatives.

—Injecting Layer—

The injecting layer is a layer which is provided between an electrode and an organic layer to reduce the driving voltage and improve the luminance. The injecting layer includes a hole-injecting layer and an electron-injecting layer and may be provided respectively between the anode and the light-emitting layer or the hole-transporting layer and between the cathode and the light-emitting layer or the electron-transporting layer. The injecting layer may be provided according to the need.

—Hole-Blocking Layer—

The hole-blocking layer has a function of the electron-transporting layer in a broad sense and is composed of a hole-blocking material which has an extremely poor ability to transport holes while having a function of transporting electrons. The hole-blocking layer can improve the probability of recombination of electrons and holes by transporting electrons while blocking holes.

It is preferable to use a 1,9-substituted carbazole compound in the hole-blocking layer. However, in the case where the said carbazole compound is used in an organic layer other than the hole-blocking layer, a known hole-blocking material may be used instead. Further, any one of the materials for the electron-transporting layer to be described later on may be used as a hole-blocking material according to the need.

—Electron-Blocking Layer—

The electron-blocking layer is made from a material which has an extremely poor ability to transport electrons while having a function of transporting holes and it can improve the probability of recombination of electrons and holes by transporting holes while blocking electrons.

As a material for the electron-blocking layer, any one of the materials for the hole-transporting layer to be described later on may be used according to the need. The thickness of the electron-blocking layer is preferably 3 to 100 nm, more preferably 5 to 30 nm.

—Exciton-Blocking Layer—

The exciton-blocking layer is a layer for blocking excitons that are generated by the recombination of holes and electrons in the light-emitting layer from diffusing to the charge-transporting layer. The insertion of this layer makes it possible to efficiently confine excitons in the light-emitting layer and enhance the luminous efficiency of the device. The exciton-blocking layer may be inserted either on the anode side or on the cathode side adjacent to the light-emitting layer or simultaneously on both the anode and the cathode sides.

Examples of a material for the exciton-blocking layer include 1,3-dicarbazolylbenzene (mCP) and bis(2-methyl-8-quinolinolato)-4-phenylphenolatoaluminum(III) (BAlq).

—Hole-Transporting Layer—

The hole-transporting layer is made from a hole-transporting material which has a function of transporting holes and it may be provided in a single layer or a plurality of layers.

The hole-transporting material has either a property of injecting or transporting holes or a property of constituting a barrier to electrons and it may be an organic substance or an inorganic substance. It is preferable to use a 1,9-substituted carbazole compound in the hole-transporting layer, but a suitable material may be selected from the known compounds and used. Specific examples of known hole-transporting materials suitable for use include triazole derivatives, oxadiazole derivatives, imidazole derivatives, polyarylalkane derivatives, pyrazoline derivatives, pyrazolone derivatives, phenylenediamine derivatives, arylamine derivatives, amino-substituted chalcone derivatives, oxazole derivatives, styrylanthracene derivatives, fluorenone derivatives, hydrazone derivatives, stilbene derivatives, silazane derivatives, aniline-based copolymers, and electrically conductive oligomers, particularly thiophene oligomers. Preferable examples include porphyrin compounds, aromatic tertiary amine compounds, and styrylamine compounds and more preferable examples include aromatic tertiary amine compounds.

—Electron-Transporting Layer—

The electron-transporting layer is made from a material which has a function of transporting electrons and may be provided in a single layer or a plurality of layers.

An electron-transporting material (serving also as a hole-blocking material in some cases) may be an arbitrary material so long as it has a function of transporting electrons that are injected from the cathode to the light-emitting layer. It is preferable to use the material represented by general formula (1) of this invention, but an arbitrary material may be selected from the known compounds and used. Examples of such known compounds include nitro-substituted fluorene derivatives, diphenylquinone derivatives, thiopyran dioxide derivatives, carbodimide, fluorenylidenemethane derivatives, anthraquinodimethan derivatives, anthrone derivatives, and oxadiazole derivatives. Further, thiadiazole derivatives which are derived from the aforementioned oxadiazole derivatives by substituting a sulfur atom for the oxygen atom of the oxadiazole ring and quinoxaline derivatives which have a quinoxaline ring known as an electron-withdrawing group may be used as electron-transporting materials. Further, polymer materials which contain any of these materials in the polymer chain or polymer materials whose backbone is constituted of any of these materials may be used.

EXAMPLES

This invention is explained in more detail hereinafter with reference to the examples. However, this invention is not limited to the examples and can be reduced to practice in various modes unless such a practice exceeds the gist of this invention.

The 1,9-substituted carbazole compounds to serve as materials for phosphorescent light-emitting devices were synthesized by the routes shown below. The compound numbers correspond to the numbers assigned to the aforementioned chemical formulas.

Synthetic Example 1

Synthesis of Compound 1

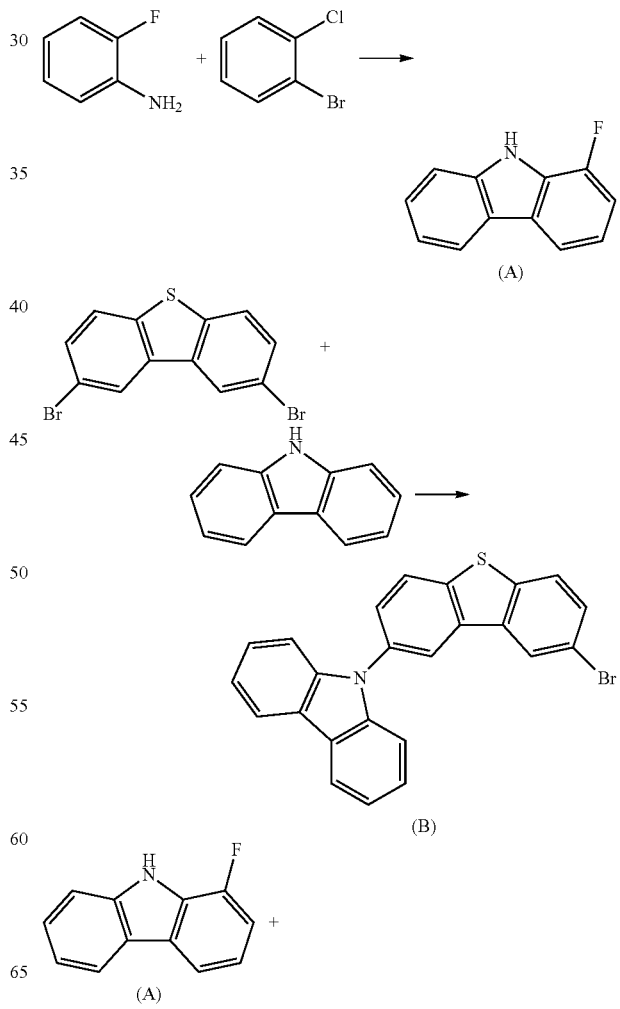

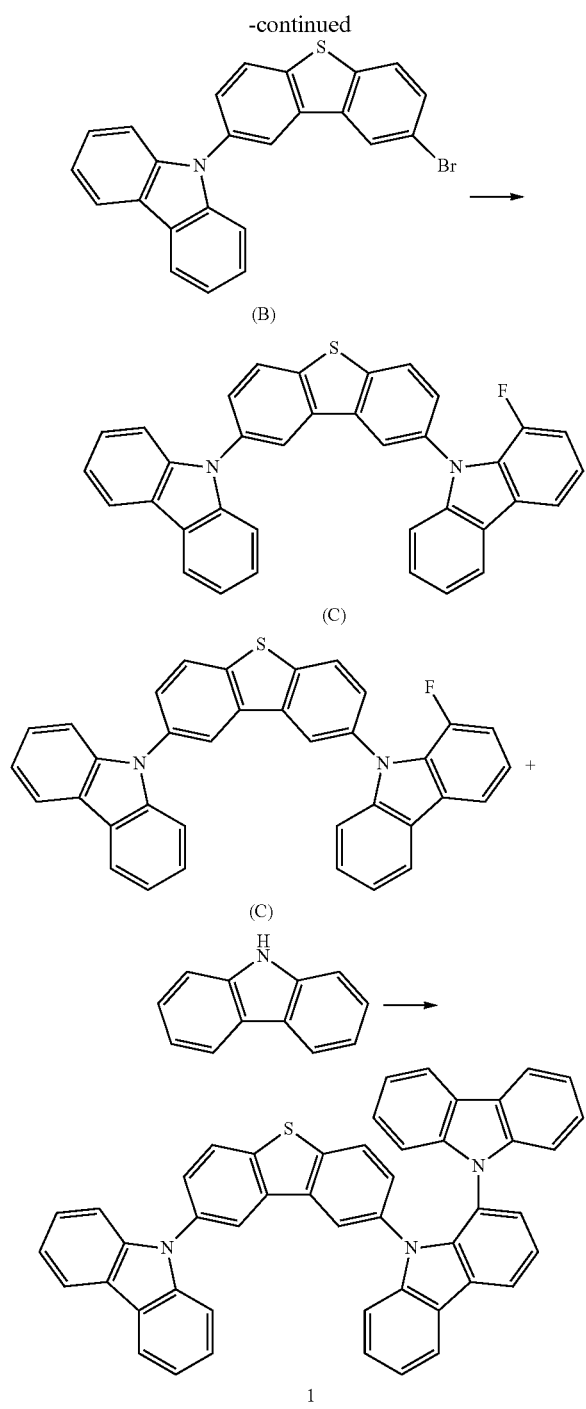

(B)

(C)

(C)

1

Under a nitrogen atmosphere, 7.0 g (0.0313 mol) of palladium acetate, 88 g (0.0626 mol) of a 20 wt % toluene solution of tricyclohexylphosphine, and 150 mL of 1-methylpyrrolidone (NMP) were stirred at 60° C. for 1 hour. To the resulting yellow solution were added 69.6 g (0.627 mol) of 1-fluoroaniline, 100 g (0.522 mol) of 1-bromochlorobenzene, 330 g (1.56 mol) of tripotassium phosphate, and 1,500 mL of NMP with stirring at room temperature. Thereafter, the mixture was stirred at 130° C. overnight. The reaction solution was cooled to room temperature, then the precipitated crystal was collected by filtration, and the solvent was distilled off under reduced pressure. The residue thus obtained was purified by silica gel column chromatography to give 19.53 g (0.105 mol, 20.2% yield) of Intermediate A as a white solid.

Under a nitrogen atmosphere, 40.0 g (0.117 mol) of 2,8-dibromodibenzothiophene, 24.0 g (0.143 mol) of carbazole, 89.1 g (0.468 mol) of copper iodide, 99.3 g (0.468 mol) of tripotassium phosphate, 56.2 mL (0.468 mol) of trans-1,2-cyclohexanediamine, and 1,000 mL of 1,4-dioxane were stirred at 120° C. for 4 hours. The reaction solution was cooled to room temperature, then the precipitated crystal was collected by filtration, and the solvent was distilled off under reduced pressure. The residue thus obtained was purified by silica gel column chromatography to give 14.7 g (34.3 mmol, 29.3% yield) of Intermediate B as a white solid.

Under a nitrogen atmosphere, 6.29 g (0.0340 mol) of Intermediate A, 9.70 g (0.0226 mol) of Intermediate B, 17.2 g (0.0904 mol) of copper iodide, 19.2 g (0.0904 mol) of tripotassium phosphate, 10.9 mL (0.0904 mol) of trans-1,2-cyclohexanediamine, and 120 mL of 1,4-dioxane were stirred at 120° C. overnight. The reaction solution was cooled to room temperature, then the precipitated crystal was collected by filtration, and the solvent was distilled off under reduced pressure. The residue thus obtained was purified by silica gel column chromatography to give 9.30 g (17.5 mmol, 77.3% yield) of Intermediate C as a white solid.

Figure 2:
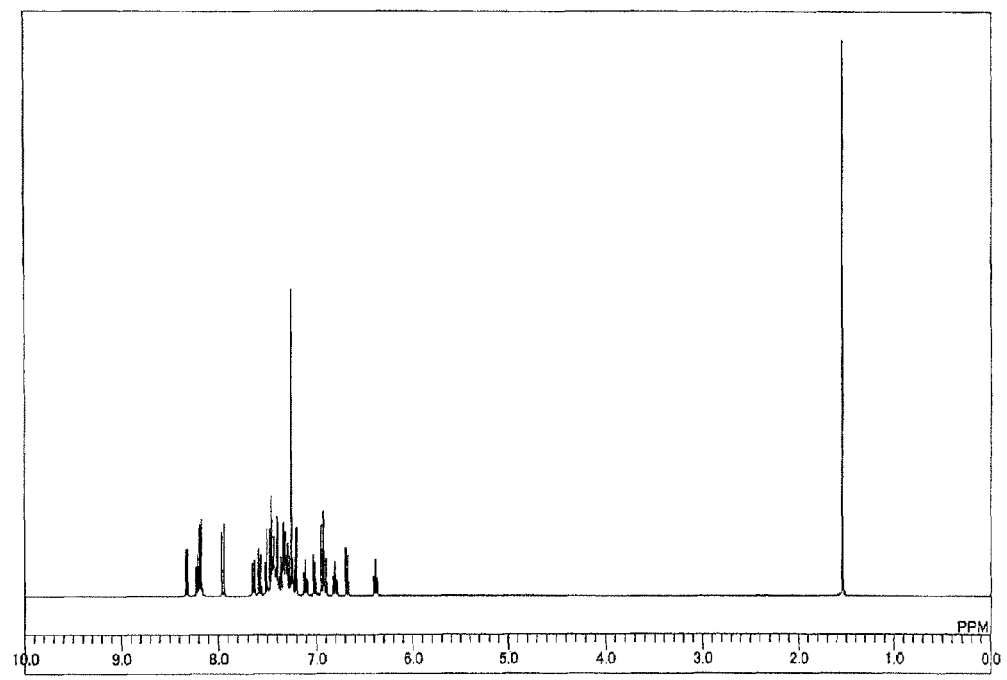
FIG. 2 shows a $^1$H-NMR chart of Compound 1.

Under a nitrogen atmosphere, 2.42 g (0.0608 mol) of sodium hydride (60.4% dispersion) and 15 mL of dehydrated N,N-dimethylformamide (DMF) were stirred at room temperature for 0.5 hour. To the resulting dispersion was added a solution of 8.48 g (0.0507 mol) of carbazole in dehydrated DMF (35.2 mL) and the mixture was stirred at room temperature for 30 minutes. To the resulting dispersion was added 9 g (0.0169 mol) of Intermediate C and the mixture was stirred at 140° C. for 4 days. The reaction solution was cooled to room temperature, then distilled water (500 mL) was added with stirring, and the precipitated light yellow solid was collected by filtration. The light yellow solid thus obtained was purified by silica gel column chromatography and reslurrying with application of heat to give 2.05 g (2.94 mmol, 17.8% yield) of Compound 1 as a white solid. APCI-TOFMS: m/z 680 [M+H]$^+$. The results of $^1$H-NMR measurement (solvent: CDCl$_3$) are shown in FIG. 2.

Synthetic Example 2

Synthesis of Compound 2

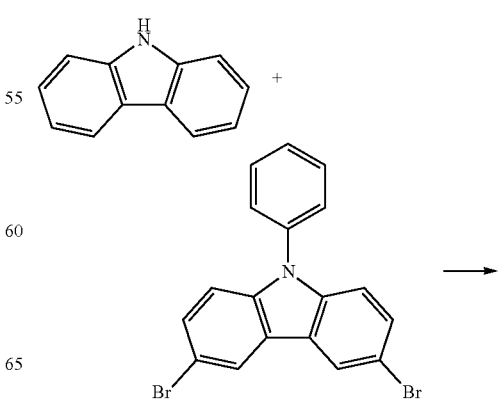

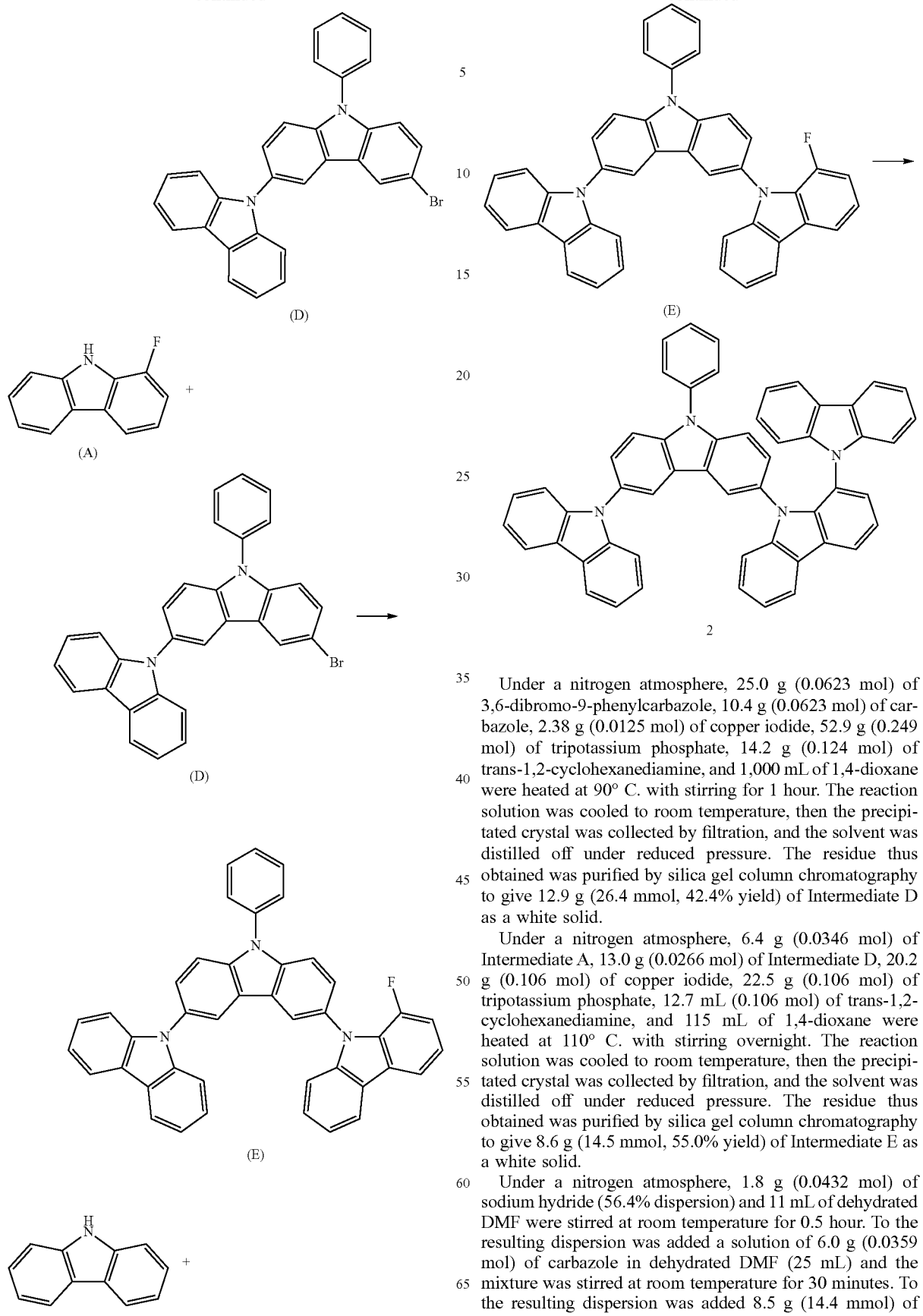

Under a nitrogen atmosphere, 25.0 g (0.0623 mol) of 3,6-dibromo-9-phenylcarbazole, 10.4 g (0.0623 mol) of carbazole, 2.38 g (0.0125 mol) of copper iodide, 52.9 g (0.249 mol) of tripotassium phosphate, 14.2 g (0.124 mol) of trans-1,2-cyclohexanediamine, and 1,000 mL of 1,4-dioxane were heated at 90° C. with stirring for 1 hour. The reaction solution was cooled to room temperature, then the precipitated crystal was collected by filtration, and the solvent was distilled off under reduced pressure. The residue thus obtained was purified by silica gel column chromatography to give 12.9 g (26.4 mmol, 42.4% yield) of Intermediate D as a white solid.

Under a nitrogen atmosphere, 6.4 g (0.0346 mol) of Intermediate A, 13.0 g (0.0266 mol) of Intermediate D, 20.2 g (0.106 mol) of copper iodide, 22.5 g (0.106 mol) of tripotassium phosphate, 12.7 mL (0.106 mol) of trans-1,2-cyclohexanediamine, and 115 mL of 1,4-dioxane were heated at 110° C. with stirring overnight. The reaction solution was cooled to room temperature, then the precipitated crystal was collected by filtration, and the solvent was distilled off under reduced pressure. The residue thus obtained was purified by silica gel column chromatography to give 8.6 g (14.5 mmol, 55.0% yield) of Intermediate E as a white solid.

Figure 3:
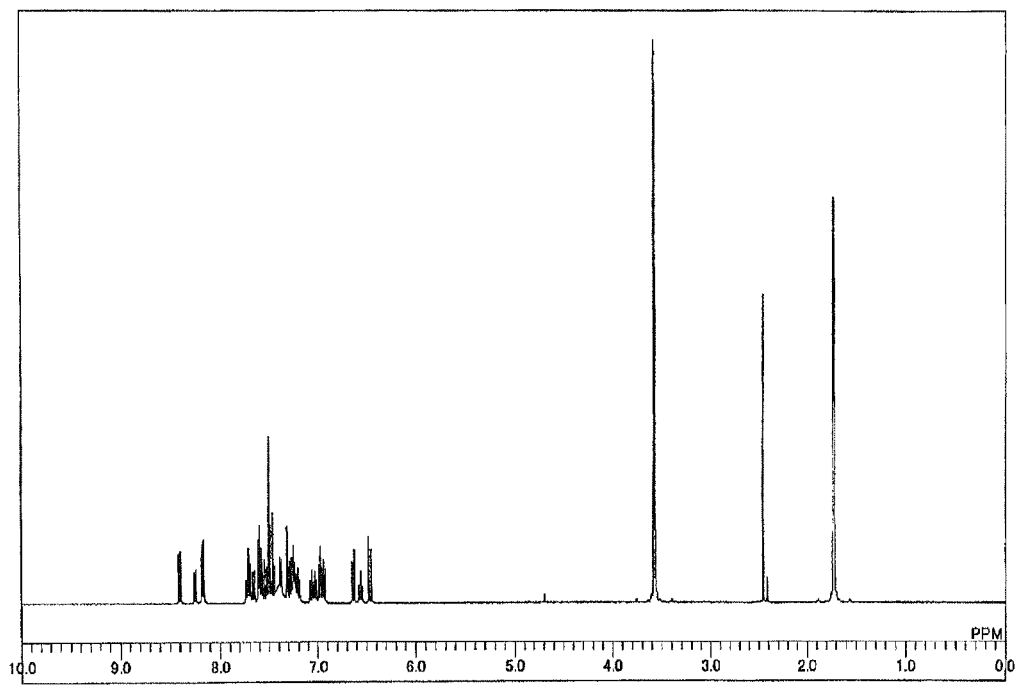
FIG. 3 shows a $^1$H-NMR chart of Compound 2.

Under a nitrogen atmosphere, 1.8 g (0.0432 mol) of sodium hydride (56.4% dispersion) and 11 mL of dehydrated DMF were stirred at room temperature for 0.5 hour. To the resulting dispersion was added a solution of 6.0 g (0.0359 mol) of carbazole in dehydrated DMF (25 mL) and the mixture was stirred at room temperature for 30 minutes. To the resulting dispersion was added 8.5 g (14.4 mmol) of Intermediate E and the mixture was stirred at 130° C. for 14 days. The reaction solution was cooled to room temperature, then distilled water (300 mL) was added with stirring, and the precipitated light yellow solid was collected by filtration. The light yellow solid thus obtained was purified by silica gel column chromatography and recrystallization to give 3.10 g (4.19 mmol, 29.0% yield) of Compound 2 as a white solid. APCI-TOFMS: m/z 739 [M+H]$^+$. The results of $^1$H-NMR measurement (solvent: CD$_2$Cl$_2$) are shown in FIG. 3.

Synthetic Example 3

Synthesis of Compound 18

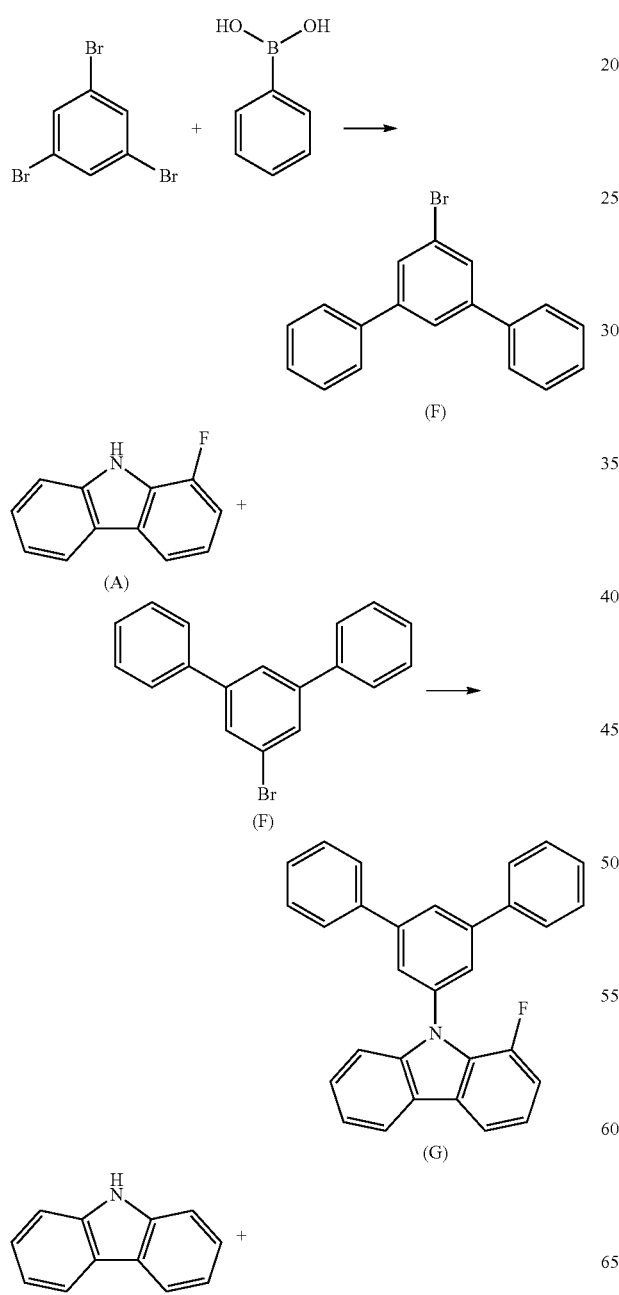

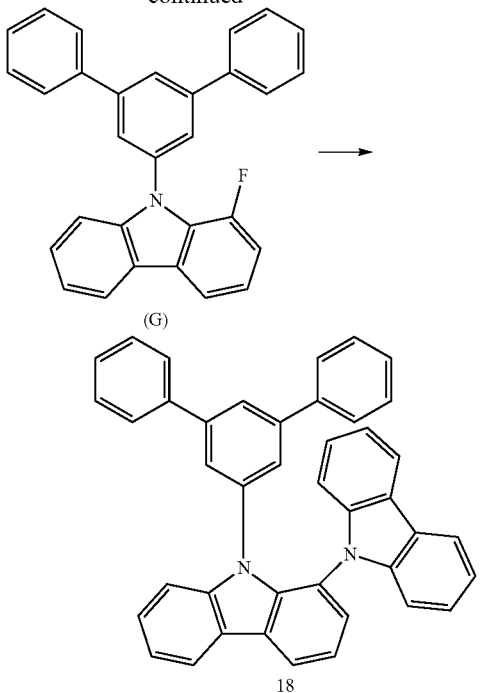

Under a nitrogen atmosphere, 69.2 g (0.219 mol) of 1,3,5-tribromobenzene, 54.5 g (0.447 mol) of phenylboronic acid, 12.0 g (0.0104 mol) of tetrakis(triphenylphosphine)palladium(0), a solution of 121 g of sodium carbonate in water (450 mL), 800 mL of toluene, and 400 mL of ethanol were stirred at 90° C. for 2 hours. The reaction solution was cooled to room temperature and then distilled water (500 mL) and toluene (500 mL) were added with stirring. The organic layer was washed with distilled water (3×500 mL). The organic layer was dried over anhydrous magnesium sulfate, the magnesium sulfate was separated by filtration, and the solvent was distilled off under reduced pressure. The residue thus obtained was purified by silica gel column chromatography to give 44.7 g (0.144 mol, 65.7% yield) of Intermediate F as a white solid.

Under a nitrogen atmosphere, 4.00 g (0.0216 mol) of Intermediate A, 10.0 g (0.0323 mol) of Intermediate F, 16.5 g (0.0864 mol) of copper iodide, 18.3 g (0.0864 mol) of tripotassium phosphate, 10.0 mL (0.0864 mol) of trans-1,2-cyclohexanediamine, and 72 mL of 1,4-dioxane were heated at 120° C. with stirring for 4 hours. The reaction solution was cooled to room temperature, then the precipitated crystal was collected by filtration, and the solvent was distilled off under reduced pressure. The residue thus obtained was purified by silica gel column chromatography to give 8.5 g (20.5 mmol, 94.9% yield) of Intermediate G as a white solid.

Figure 4:
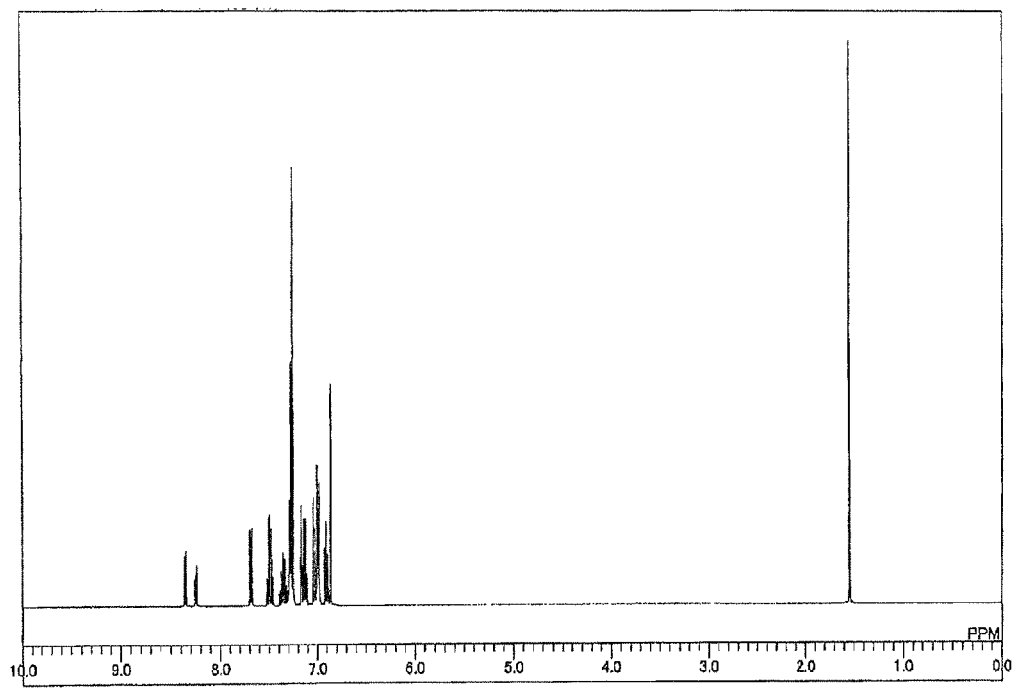
FIG. 4 shows a $^1$H-NMR chart of Compound 18.

Under a nitrogen atmosphere, 3.3 g (0.0785 mol) of sodium hydride (56.4% dispersion) and 20 mL of dehydrated DMF were stirred at room temperature for 0.5 hour. To the resulting dispersion was added a solution of 10.9 g (0.0654 mol) of carbazole in dehydrated DMF (45.4 mL) and the mixture was stirred at room temperature for 30 minutes. To the resulting dispersion was added 8.5 g (20.5 mmol) of Intermediate G and the mixture was stirred at 130° C. for 3 days. The reaction solution was cooled to room temperature, then distilled water (200 mL) was added with stirring, and the precipitated light yellow solid was collected by filtration. The light yellow solid thus obtained was purified by silica gel column chromatography and reslurrying with application of heat to give 2.70 g (4.81 mmol, 22.0% yield) of Compound 18 as a white solid. APCI-TOFMS: m/z 561 [M+H]$^+$. The results of $^1$H-NMR measurement (solvent: CDCl$_3$) are shown in FIG. 4.

Synthetic Example 4

Synthesis of Compound 82

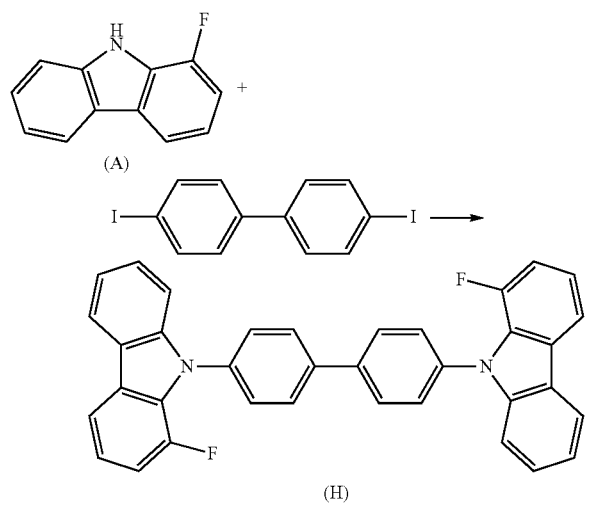

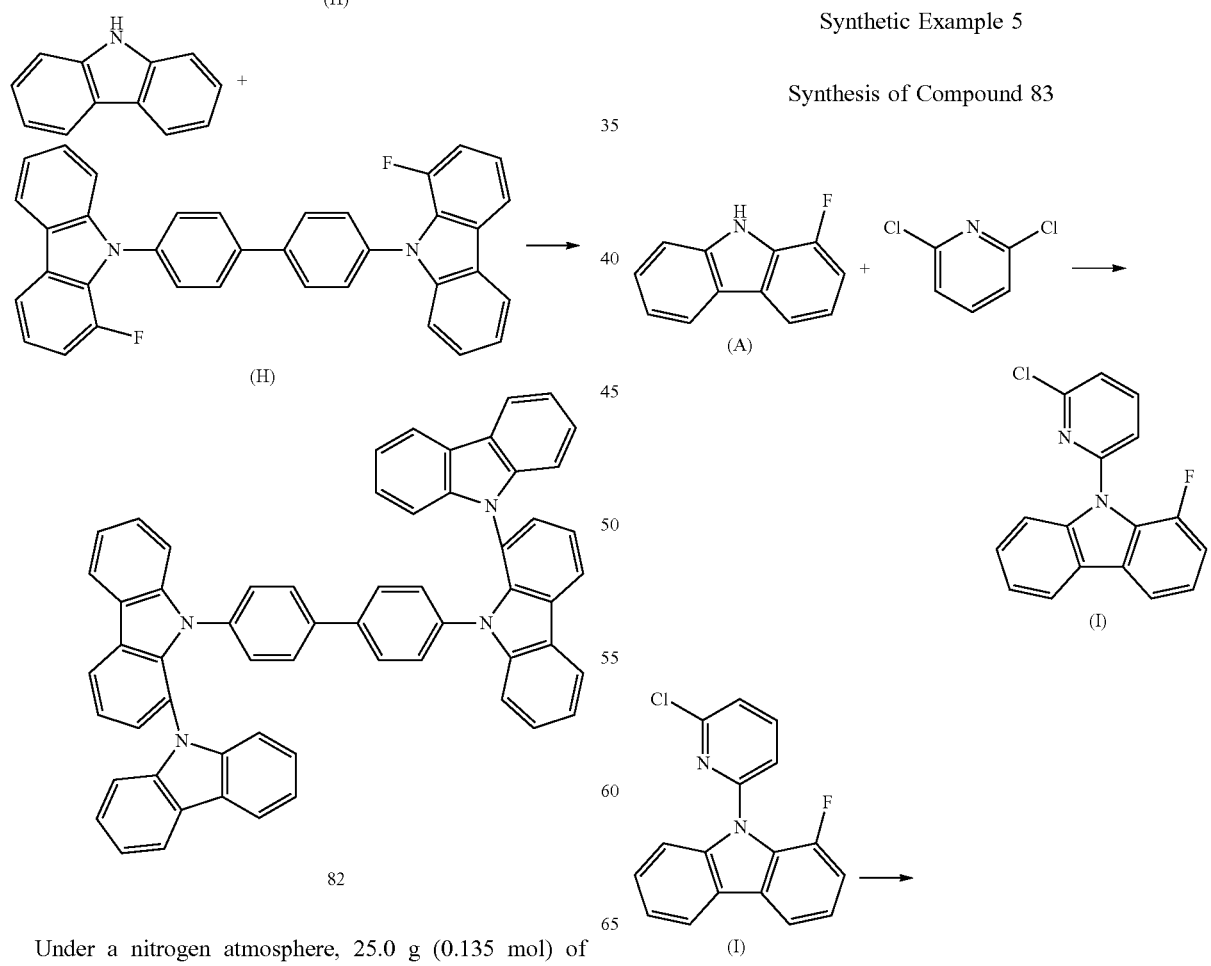

Under a nitrogen atmosphere, 25.0 g (0.135 mol) of Intermediate A, 21.0 g (0.0519 mol) of 4,4'-diiodobiphenyl, 39.5 g (0.207 mol) of copper iodide, 43.9 g (0.207 mol) of tripotassium phosphate, 25.0 mL (0.207 mol) of trans-1,2-cyclohexanediamine, and 450 mL of 1,4-dioxane were heated at 120° C. with stirring for 18 hours. The reaction solution was cooled to room temperature, then the precipitated crystal was collected by filtration, and the solvent was distilled off under reduced pressure. The residue thus obtained was purified by silica gel column chromatography to give 10.4 g (20.1 mmol, 38.7% yield) of Intermediate H as a white solid.

Figure 5:
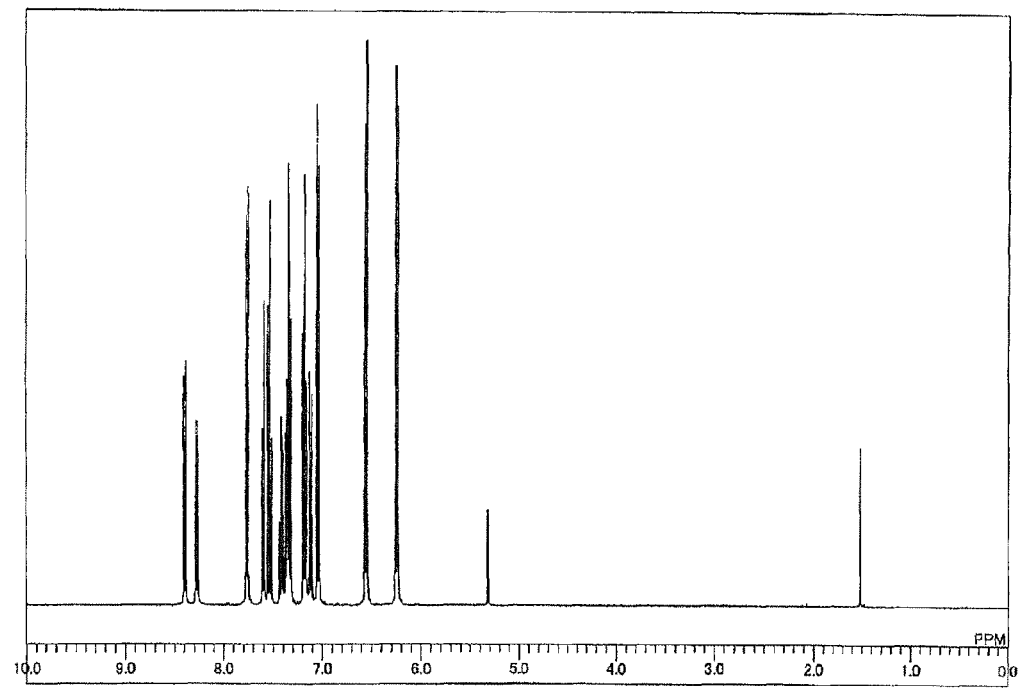
FIG. 5 shows a $^1$H-NMR chart of Compound 82.

Under a nitrogen atmosphere, 4.9 g (0.115 mol) of sodium hydride (56.4% dispersion) and 30 mL of dehydrated DMF were stirred at room temperature for 0.5 hour. To the resulting dispersion was added a solution of 16.0 g (0.0960 mol) of carbazole in dehydrated DMF (60 mL) and the mixture was stirred at room temperature for 30 minutes. To the resulting dispersion was added 10.0 g (19.2 mmol) of Intermediate H and the mixture was stirred at 130° C. for 6 days. The reaction solution was cooled to room temperature, then distilled water (200 mL) was added with stirring, and the precipitated light yellow solid was collected by filtration. The light yellow solid thus obtained was purified by silica gel column chromatography and recrystallization to give 2.40 g (2.94 mmol, 15.3% yield) of Compound 82 as a white solid. APCI-TOFMS: m/z 815 [M+H]$^+$. The results of $^1$H-NMR measurement (solvent: CD$_2$Cl$_2$) are shown in FIG. 5.

Synthetic Example 5

Synthesis of Compound 83

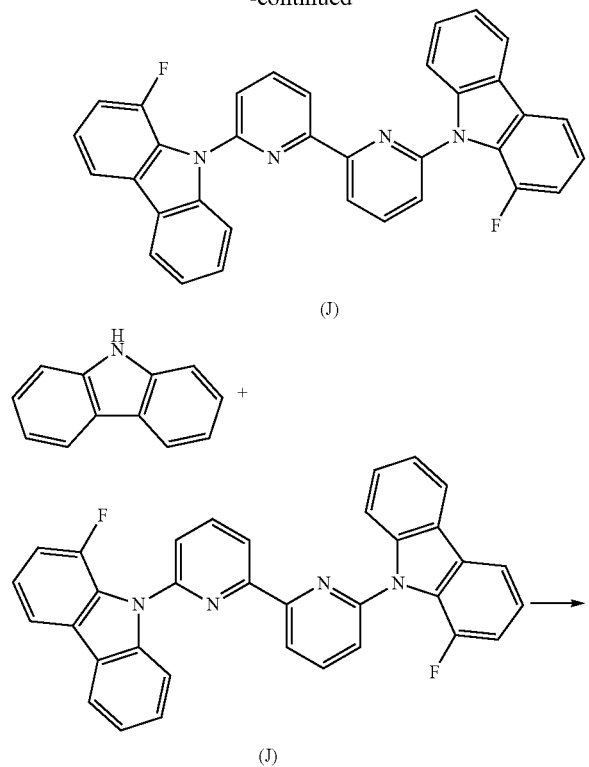

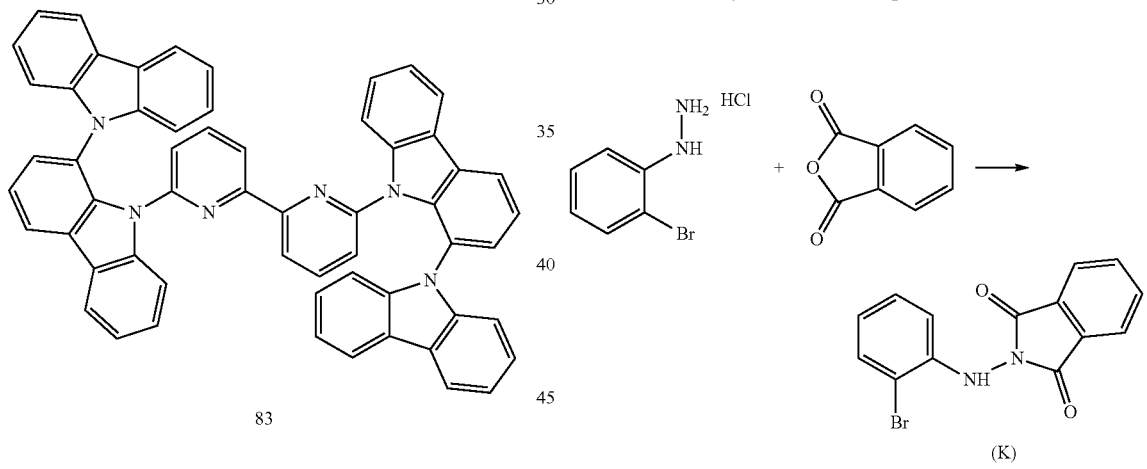

Under a nitrogen atmosphere, 43.0 g (0.232 mol) of Intermediate A, 41.0 g (0.277 mol) of 2,6-dichloropyridine, 82.0 g (0.431 mol) of copper iodide, 92.0 g (0.433 mol) of tripotassium phosphate, 50.0 mL (0.416 mol) of trans-1,2-cyclohexanediamine, and 500 mL of 1,4-dioxane were heated at 110° C. with stirring for 6 hours. The reaction solution was cooled to room temperature, then the precipitated crystal was collected by filtration, and the solvent was distilled off under reduced pressure. The residue thus obtained was purified by silica gel column chromatography to give 40.4 g (0.136 mol, 74.9% yield) of Intermediate I as a white solid.

Under a nitrogen atmosphere, 38.4 g (0.161 mol) of nickel chloride hexahydrate, 195.0 g (0.743 mol) of triphenylphosphine, and 500 mL of dehydrated DMF were heated at 60° C. for 20 minutes. Thereafter, 14.8 g (0.214 mol) of zinc powder was added and the mixture was heated at 60° C. for 2 hours. To the resulting dispersion was added a solution of 40.0 g (0.134 mol) of Intermediate I in dehydrated DMF (90 mL) and the mixture was stirred at 60° C. for 1 hour. The reaction solution was cooled to room temperature, then a 10% aqueous ammonia solution (1,000 mL) was added with stirring, and the precipitated gray solid was collected by filtration. The grey solid thus obtained was purified by crystallization to give 20.4 g (39.0 mmol, 29.1% yield) of Intermediate J as a white solid.

Figure 6:
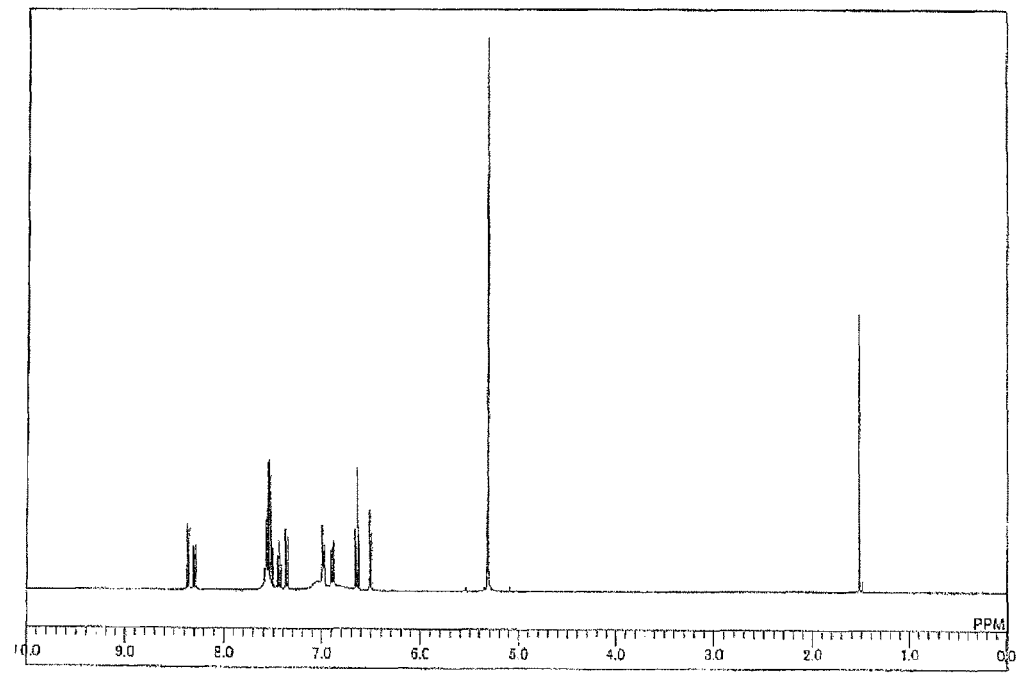
FIG. 6 shows a $^1$H-NMR chart of Compound 83.

Under a nitrogen atmosphere, 4.4 g (0.115 mol) of sodium hydride (62.0% dispersion) and 30 mL of dehydrated DMF were stirred at room temperature for 0.5 hour. To the resulting dispersion was added a solution of 15.9 g (0.0955 mol) of carbazole in dehydrated DMF (66 mL) and the mixture was stirred at room temperature for 30 minutes. To the resulting dispersion was added 10.0 g (21.1 mmol) of Intermediate J and the mixture was stirred at 130° C. for 7 days. Two batches of this reaction solution were cooled to room temperature, then distilled water (500 mL) was added with stirring, and the precipitated gray solid was collected by filtration. The gray solid thus obtained was purified by crystallization to give 2.10 g (2.57 mmol, 6.71% yield) of Compound 83 as a white solid. APCI-TOFMS: m/z 817 [M+H]$^+$. The results of $^1$H-NMR measurement (solvent: CD$_2$Cl$_2$) are shown in FIG. 6.

Synthetic Example 6

Synthesis of Compound H-1

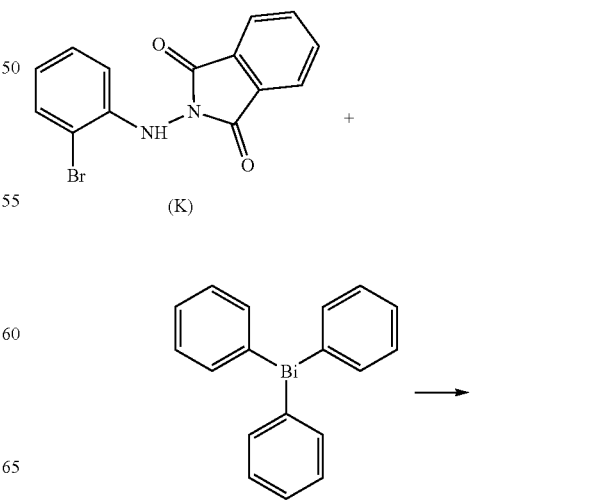

-continued

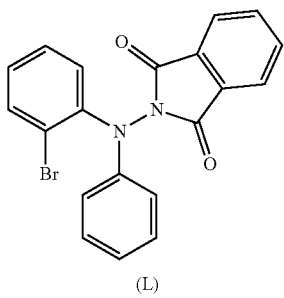

(L)

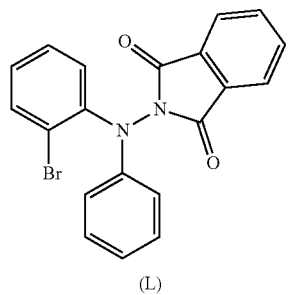

(L)

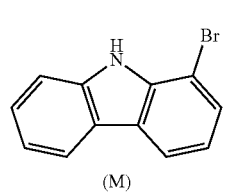 + 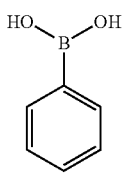

(M)

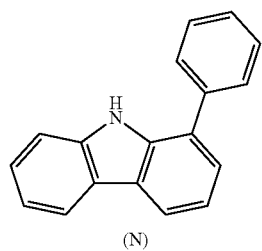

(N)

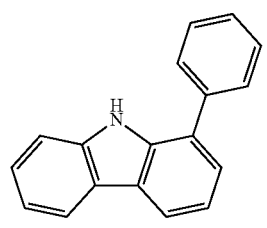 +

(N)

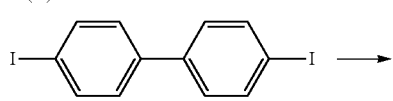

-continued

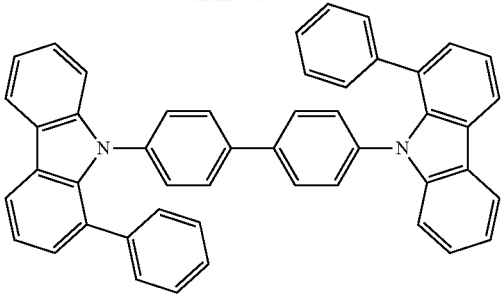

H-1

Under a nitrogen atmosphere, 150 g (0.801 mol) of 2-bromophenylhydrazine hydrochloride, 190 g (1.28 mol) of phthalic anhydride, and 4,500 mL of toluene were heated at 120° C. with stirring overnight. The reaction solution was cooled to room temperature and then the precipitated light yellow solid was collected by filtration. The light yellow solid thus obtained was purified by reslurrying with application of heat to give 181 g (0.570 mol, 71.1% yield) of Intermediate K as a light yellow powder.

Under a nitrogen atmosphere, 126 g (0.397 mol) of Intermediate K, 350 g (0.794 mol) of triphenylbismuthine, 108 g (0.596 mol) of copper acetate, and 3,000 mL of dehydrated methylene chloride were stirred in an ice bath. Then, 41.3 mL (0.298 mol) of triethylamine was added slowly so as not to raise the internal temperature above 5° C. and then the mixture was heated at 50° C. with stirring overnight. The reaction solution was cooled to room temperature, then the precipitated light yellow solid was collected by filtration, and the light yellow solid thus obtained was purified by recrystallization to give 72.0 g (0.183 mol, 45.2% yield) of Intermediate L as a light yellow solid.

Under a nitrogen atmosphere, 30.0 g (0.0762 mol) of Intermediate L was mixed with 1,500 mL of dehydrated benzene, 50.8 g (0.381 mol) of aluminum chloride was added at room temperature with stirring, and then the mixture was stirred at room temperature for 3 hours. To the mixture was added 900 mL of an aqueous sodium hydroxide solution with stirring. The reaction solution was cooled to room temperature and then distilled water (1,000 mL) and toluene (1,000 mL) were added with stirring. The organic layer was washed with distilled water (3×1,000 mL). The organic layer was dried over anhydrous magnesium sulfate, the magnesium sulfate was separated by filtration, and the solvent was distilled off under reduced pressure. The residue thus obtained was purified by silica gel column chromatography to give 8.0 g (0.0325 mol, 42.6% yield) of Intermediate M as a white solid.

Under a nitrogen atmosphere, 8.8 g (0.0325 mol) of Intermediate M, 8.7 g (0.0715 mol) of phenylboronic acid, 3.3 g (2.86 mmol) of tetrakis(triphenylphosphine)palladium (0), a solution of 13.6 g of sodium carbonate in water (60 mL), 180 mL of toluene, and 60 mL of ethanol were heated at 90° C. with stirring overnight. The reaction solution was cooled to room temperature and distilled water (300 mL) was added with stirring. The organic layer was washed with distilled water (3×300 mL). The organic layer was dried over anhydrous magnesium sulfate, the magnesium sulfate was separated by filtration, and the solvent was distilled off under reduced pressure. The residue thus obtained was purified by silica gel column chromatography to give 7.0 g (28.7 mmol, 80.3% yield) of Intermediate N as a white solid.

Figure 7:
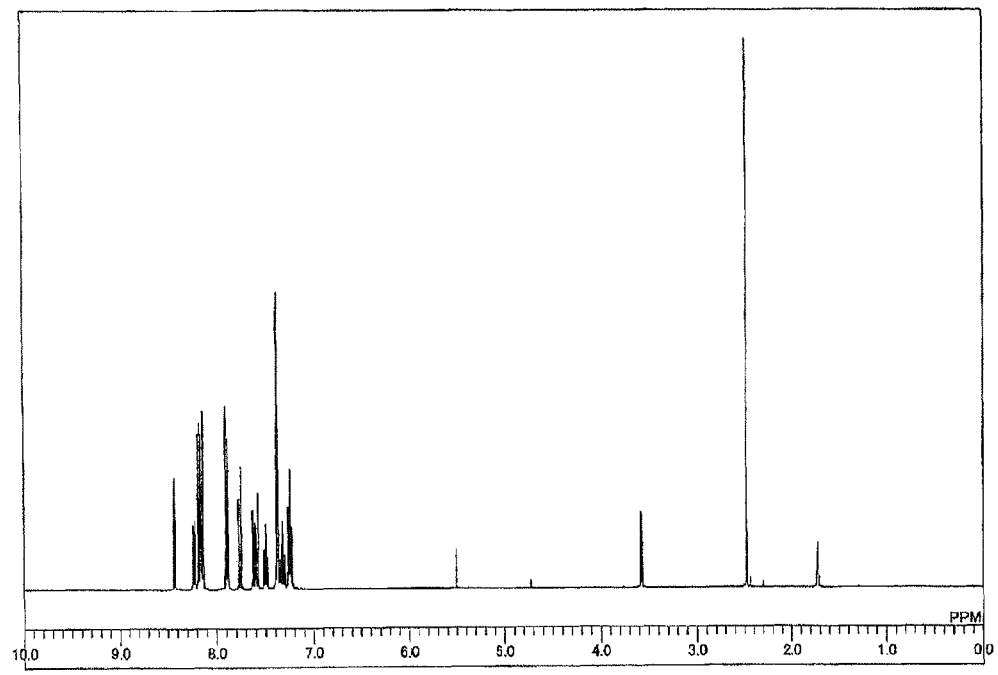
FIG. 7 shows a $^1$H-NMR chart of Compound H-1.

Under a nitrogen atmosphere, 7.0 g (0.0288 mol) of Intermediate N, 5.3 g (0.0131 mol) of 4,4'-diiodobiphenyl, 1.24 g (6.55 mmol) of copper iodide, 14.5 g (0.104 mol) of potassium carbonate, and 50 mL of quinoline were heated at 260° C. with stirring for 5 hours. The reaction solution was cooled to room temperature and then the precipitated black solid was collected by filtration. The black solid thus obtained was purified by crystallization to give 4.0 g (6.28 mmol, 47.9% yield) of Compound H-1 as a white solid. APCI-TOFMS: m/z 637 [M+H]$^+$. The results of $^1$H-NMR measurement (solvent: THF-d$_8$) are shown in FIG. 7.

Synthetic Example 7

Synthesis of Compound H-2

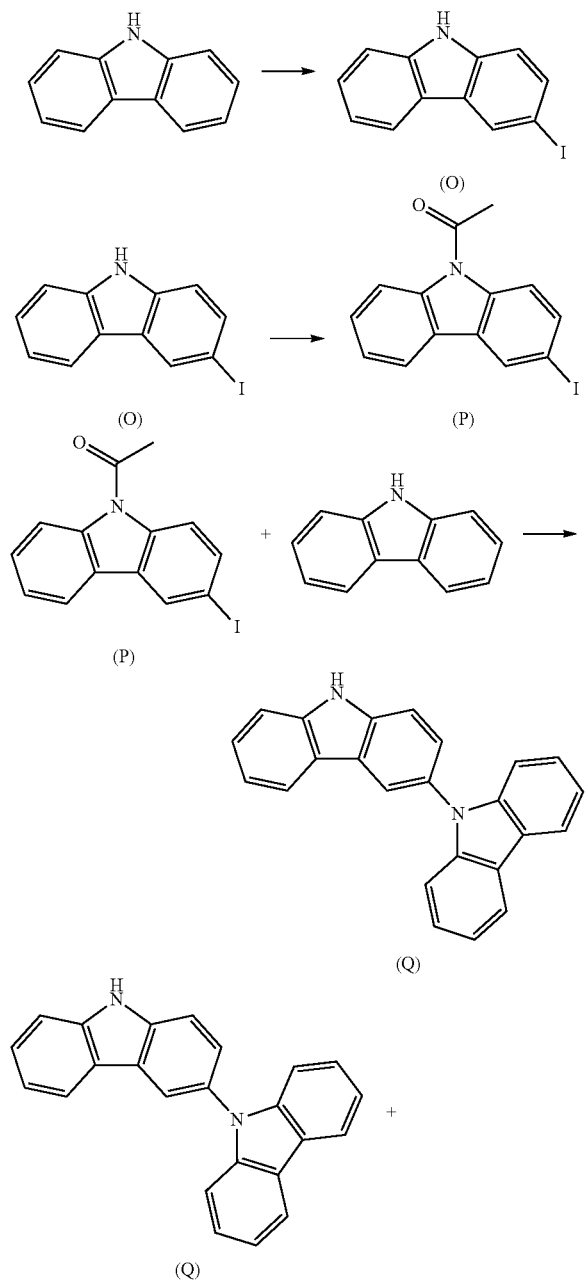

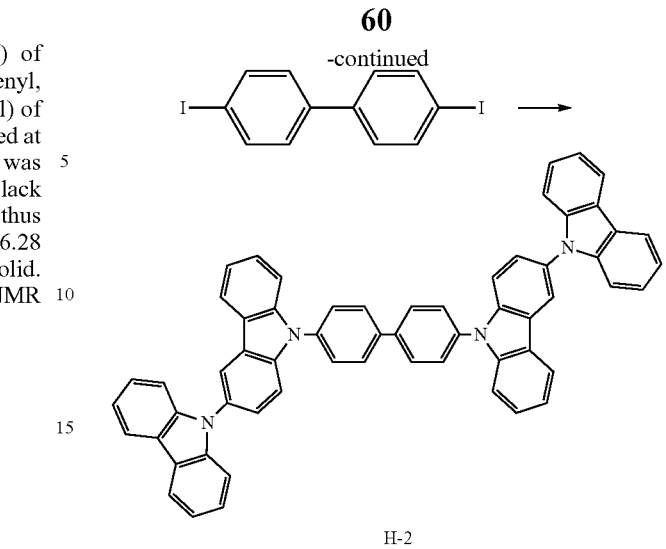

H-2

Under a nitrogen atmosphere, 60.0 g (0.358 mol) of carbazole was mixed with 840 mL of acetic acid, 41.6 g (0.250 mol) of potassium iodide and 53.6 g (0.250 mol) of hydroiodic acid were added with stirring, and the mixture was heated at 80° C. with stirring for 4 hours. The reaction solution was cooled to room temperature, then distilled water (1,000 mL) was added with stirring, and the precipitated light yellow solid was collected by filtration. The light yellow solid thus obtained was purified by reslurrying with application of heat to give 50.0 g (0.170 mol, 47.6% yield) of Intermediate O as a white solid.

Under a nitrogen atmosphere, 50.0 g (0.170 mol) of Intermediate O was mixed with 215 mL (2.21 mol) of acetic anhydride, 0.64 mL (5.10 mmol) of boron trifluoride diethyl ether complex was added with ice cooling and stirring, and the mixture was heated at 80° C. with stirring for 0.5 hour. The reaction solution was cooled to room temperature, then distilled water (500 mL) was added with stirring, and the precipitated light yellow solid was collected by filtration. The light yellow solid thus obtained was purified by reslurrying to give 45.0 g (0.134 mol, 78.9% yield) of Intermediate P as a light yellow solid.

Under a nitrogen atmosphere, 45.0 g (0.134 mol) of Intermediate P, 24.7 g (0.147 mol) of carbazole, 57.5 g (0.402 mol) of copper oxide, and 1,000 mL of dimethylacetamide were heated at 160° C. with stirring for 3 days. The reaction solution was cooled to room temperature, then distilled water (1,000 mL) was added with stirring, and the organic layer was washed with distilled water (3×500 mL). The organic layer was dried over anhydrous magnesium sulfate, the magnesium sulfate was separated by filtration, and the solvent was distilled off under reduced pressure. To the residue thus obtained were added 200 mL of tetrahydrofuran, 100 mL of dimethyl sulfoxide, 33 g (0.588 mol) of potassium hydroxide, and 10 mL of distilled water and the mixture was heated at 80° C. with stirring for 2 hours. The reaction solution was cooled to room temperature, toluene (1,000 mL) and distilled water (500 mL) were added with stirring, and the organic layer was washed with distilled water (3×500 mL). The organic layer was dried over anhydrous magnesium sulfate, the magnesium sulfate was separated by filtration, and the solvent was distilled off under reduced pressure. The residue thus obtained was purified by silica gel column chromatography to give 21.2 g (63.7 mmol, 47.5% yield) of Intermediate Q as a white solid.

Figure 8:
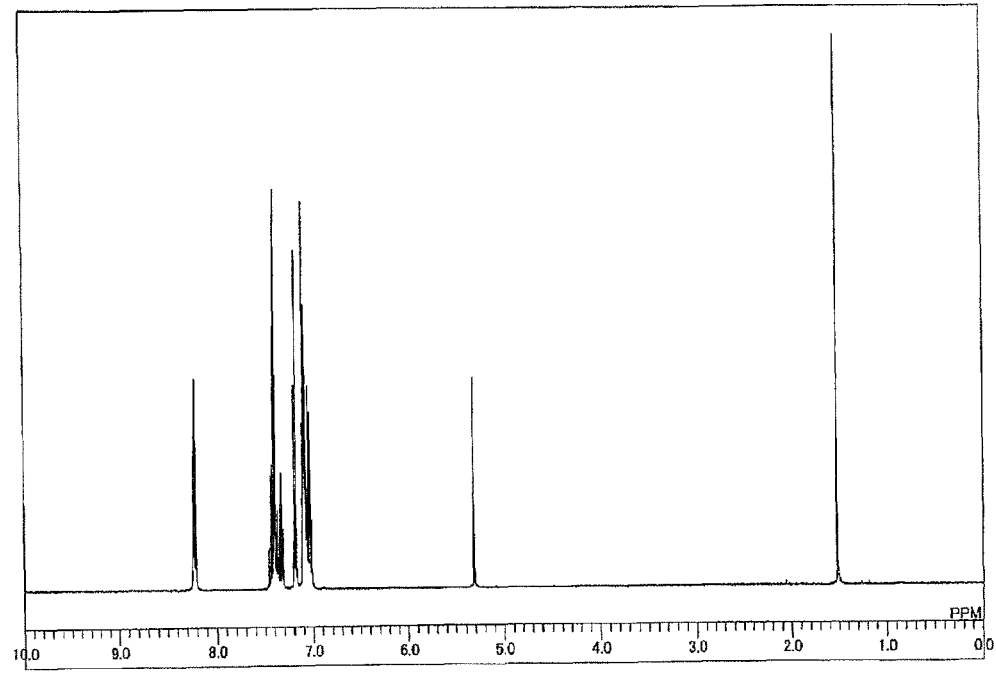
FIG. 8 shows a $^1$H-NMR chart of Compound H-2.

Under a nitrogen atmosphere, 10.0 g (0.0300 mol) of Intermediate Q, 4.69 g (0.0116 mol) of 4,4'-diiodobiphenyl, 8.84 g (0.0464 mol) of copper iodide, 9.84 g (0.0464 mol) of tripotassium phosphate, 5.6 mL (0.0464 mol) of trans-1,2-cyclohexanediamine, and 100 mL of 1,4-dioxane were heated at 120° C. with stirring for 6 hours. The reaction solution was cooled to room temperature, then the precipitated crystal was collected by filtration, and the solvent was distilled off under reduced pressure. The residue thus obtained was purified by crystallization and silica gel column chromatography to give 2.2 g (2.69 mmol, 23.1% yield) of Compound H-2 as a white solid. APCI-TOFMS: m/z 815 [M+H]$^+$. The results of $^1$H-NMR measurement (solvent: $CD_2Cl_2$) are shown in FIG. 8.

Compounds 4, 22, 57, and 87 were synthesized according to the methods described in the aforementioned Synthetic Examples and in the specification and used in the fabrication of organic EL devices.

The calculated values of the T1 energy of the compounds prepared in the aforementioned Synthetic Examples and of CBP are shown in Table 1. The calculation was made by using the aforementioned Gaussian 03. Here, CBP, Compound H-1, and Compound H-2 are shown for the sake of comparison. Table 1 confirms that the introduction of a substituent composed of two rings or more to the 1 position increases the T1 energy.

TABLE 1

| Compound | T1 energy (eV) |
|---|---|
| 1 | 3.08 |
| 18 | 3.12 |
| 82 | 3.13 |
| CBP | 2.95 |
| H-1 | 3.04 |
| H-2 | 3.00 |

Example 1

The constituent layers were deposited in thin film by the vacuum deposition process at a degree of vacuum of 2.0× 10$^{-5}$ Pa one upon another on a glass substrate on which a 110 nm-thick indium tin oxide (ITO) anode had been formed. First, copper phthalocyanine (CuPc) was deposited on the ITO anode to a thickness of 25 nm as a hole-injecting layer and then N,N'-di(naphthalen-1-yl)-N,N'-diphenyl-benzidine (NPB) was deposited to a thickness of 90 nm as a hole-transporting layer. Next, Compound 1 as a host material and iridium(III)bis[(4,6-difluorophenyl)-pyridinato-N,C2']picolinate (FIrpic), a phosphorescent blue light emitter, as a dopant were co-deposited from different deposition sources to a thickness of 30 nm as a light-emitting layer. The concentration of FIrpic was 10%. Next, Alq3 was deposited to a thickness of 30 nm as an electron-transporting layer. Further, lithium fluoride (LiF) was deposited on the electron-transporting layer to a thickness of 1.0 nm as an electron-injecting layer. Finally, aluminum (Al) as an electrode was deposited on the electron-injecting layer to a thickness of 70 nm. The organic EL device thus fabricated has a layered structure formed by inserting an electron-injecting layer between the cathode and the electron-transporting layer in FIG. 1

Each of the organic EL devices thus fabricated was connected to an external power source and, when direct current voltage was applied, the device was confirmed to have the luminous characteristics shown in Table 2. In Table 2, the values of the luminance, voltage, and luminous efficiency are values obtained when the device was driven at 2.5 mA/cm$^2$. The peak wavelength of the spectrum of light emitted from the device is 475 nm and this proves that light is emitted from FIrpic.

Example 2

An organic EL device was fabricated as in Example 1 except that Compound 2 was used as the host material in the light-emitting layer in Example 1.

Example 3

An organic EL device was fabricated as in Example 1 except that Compound 4 was used as the host material in the light-emitting layer in Example 1.

Example 4

An organic EL device was fabricated as in Example 1 except that Compound 18 was used as the host material in the light-emitting layer in Example 1.

Example 5

An organic EL device was fabricated as in Example 1 except that Compound 22 was used as the host material in the light-emitting layer in Example 1.

Example 6

An organic EL device was fabricated as in Example 1 except that Compound 57 was used as the host material in the light-emitting layer in Example 1.

Example 7

An organic EL device was fabricated as in Example 1 except that Compound 82 was used as the host material in the light-emitting layer in Example 1.

Example 8

An organic EL device was fabricated as in Example 1 except that Compound 83 was used as the host material in the light-emitting layer in Example 1.

Example 9

An organic EL device was fabricated as in Example 1 except that Compound 87 was used as the host material in the light-emitting layer in Example 1.

Comparative Example 1

An organic EL device was fabricated as in Example 1 except that CBP was used as the host material in the light-emitting layer in Example 1.

Comparative Example 2

An organic EL device was fabricated as in Example 1 except that Compound H-1 was used as the host material in the light-emitting layer in Example 1.

Comparative Example 3

An organic EL device was fabricated as in Example 1 except that Compound H-2 was used as the host material in the light-emitting layer in Example 1.

The organic EL devices fabricated in Examples 2 to 9 and Comparative Examples 1 to 3 were evaluated as in Example 1 and they were confirmed to have the luminous characteristics shown in Table 2. The peak wavelength of the spectrum of light emitted from each of the organic EL devices fabricated in Examples 2 to 9 and Comparative Examples 1 and 2 was 475 nm and it was identified that light is emitted from FIrpic. On the other hand, the peak wavelength of the spectrum of light emitted from the organic EL device fabricated in Comparative Example 3 was 505 nm and the object emission of light was not obtained.

TABLE 2

| | | Initial characteristics (@2.5 mA/cm$^2$) | | |
|---|---|---|---|---|
| | Compound | Luminance (cd/m$^2$) | Voltage (V) | Luminous efficiency (lm/W) |
| Example 1 | 1 | 142 | 8.0 | 2.2 |
| 2 | 2 | 144 | 8.2 | 2.2 |
| 3 | 4 | 140 | 8.1 | 2.2 |
| 4 | 18 | 128 | 8.1 | 2.0 |
| 5 | 22 | 143 | 8.2 | 2.2 |
| 6 | 57 | 144 | 8.2 | 2.2 |
| 7 | 82 | 139 | 8.5 | 2.1 |
| 8 | 83 | 135 | 7.5 | 2.3 |
| 9 | 87 | 145 | 8.3 | 2.1 |
| Comparative Example 1 | CBP | 91 | 8.5 | 1.3 |
| 2 | H-1 | 105 | 8.7 | 1.5 |
| 3 | H-2 | 47 | 7.2 | 0.8 |

It is apparent from Table 2 that the use of the 1,9-substituted carbazole compound in the light-emitting layer in each of Examples 1 to 9 leads to display of higher luminous characteristics than in other cases (Comparative Examples 1, 2, and 3). This is due to the effects of control of extension of the molecular orbitals and optimization of the balance of electric charges caused by the introduction of a fused-ring substituent composed of two rings or more to the 1 position of carbazole and proves the superior performance of the 1,9-substituted carbazole derivatives. These results clearly indicate that the use of the aforementioned carbazole compounds in the light-emitting layer realizes organic EL devices of high efficiency.

Example 10

The constituent layers were deposited in thin film by the vacuum deposition process at a degree of vacuum of 2.0× 10$^{-5}$ Pa one upon another on a glass substrate on which a 110 nm-thick indium tin oxide (ITO) anode had been formed. First, copper phthalocyanine (CuPc) was deposited on the ITO anode to a thickness of 25 nm as a hole-injecting layer and then NPB was deposited to a thickness of 40 nm as a hole-transporting layer. Next, Compound 1 as a host material and Ir(ppy)$_3$ as a dopant were co-deposited from different deposition sources to a thickness of 40 nm as a light-emitting layer. At this time, the concentration of Ir(ppy)$_3$ was 10 wt %. Next, Alq3 was deposited to a thickness of 20 nm as an electron-transporting layer. Further, lithium fluoride (LiF) was deposited on the electron-transporting layer to a thickness of 1 nm as an electron-injecting layer. Finally, aluminum (Al) as an electrode was deposited on the electron-injecting layer to a thickness of 70 nm to complete the fabrication of an organic EL device.

The organic EL device thus fabricated was connected to an external power source and, when direct current voltage was applied, the device was confirmed to have the luminous characteristics shown in Table 3. In Table 3, the values of the luminance, voltage, and luminous efficiency are values obtained when the device was driven at 20 mA/cm$^2$. The luminance half-life was evaluated by driving the device by constant current at 20 mA/cm$^2$ and the results were converted to the case where the initial luminance was 1,000 cd/m$^2$. The peak wavelength of the spectrum of light emitted from the device is 530 nm and this proves that light is emitted from Ir(ppy)$_3$.

Example 11

An organic EL device was fabricated as in Example 10 except that Compound 2 was used as the host material in the light-emitting layer in Example 10.

Example 12

An organic EL device was fabricated as in Example 10 except that Compound 4 was used as the host material in the light-emitting layer in Example 10.

Example 13

An organic EL device was fabricated as in Example 10 except that Compound 18 was used as the host material in the light-emitting layer in Example 10.

Example 14

An organic EL device was fabricated as in Example 10 except that Compound 22 was used as the host material in the light-emitting layer in Example 10.

Example 15

An organic EL device was fabricated as in Example 10 except that Compound 57 was used as the host material in the light-emitting layer in Example 10.

Example 16

An organic EL device was fabricated as in Example 10 except that Compound 82 was used as the host material in the light-emitting layer in Example 10.

Example 17

An organic EL device was fabricated as in Example 10 except that Compound 83 was used as the host material in the light-emitting layer in Example 10.

Example 18

An organic EL device was fabricated as in Example 10 except that Compound 87 was used as the host material in the light-emitting layer in Example 10.

Comparative Example 4

An organic EL device was fabricated as in Example 10 except that CBP was used as the host material in the light-emitting layer in Example 10.

Comparative Example 5

An organic EL device was fabricated as in Example 10 except that Compound H-1 was used as the host material in the light-emitting layer in Example 10.

Comparative Example 6

An organic EL device was fabricated as in Example 10 except that Compound H-2 was used as the host material in the light-emitting layer in Example 10.

The organic EL devices fabricated in Examples 11 to 18 and Comparative Examples 4 to 6 were evaluated as in Example 10 and they were confirmed to have the luminous characteristics shown in Table 3. The peak wavelength of the spectrum of light emitted from each of the organic EL devices fabricated in Examples 11 to 18 and Comparative Examples 4 to 6 was 530 nm and it was identified that light is emitted from Ir(ppy)$_3$.

TABLE 3

| | | Initial characteristics (@20 mA/cm$^2$) | | | Life characteristics |
| | Compound | Luminance (cd/m$^2$) | Voltage (V) | Luminous efficiency (lm/W) | (@1000 cd/m$^2$) Luminance half time (h) |
|---|---|---|---|---|---|
| Example 10 | 1 | 2010 | 9.1 | 3.5 | 1500 |
| 11 | 2 | 2100 | 9.2 | 3.6 | 1600 |
| 12 | 4 | 2000 | 9.0 | 3.5 | 1500 |
| 13 | 18 | 1850 | 9.1 | 3.2 | 1500 |
| 14 | 22 | 1960 | 9.3 | 3.3 | 1500 |
| 15 | 57 | 2200 | 9.3 | 3.7 | 1500 |
| 16 | 82 | 1500 | 9.2 | 2.6 | 1300 |
| 17 | 83 | 2300 | 8.5 | 4.3 | 1800 |
| 18 | 87 | 2210 | 9.1 | 3.8 | 1600 |
| Comparative Example 4 | CBP | 1120 | 8.7 | 2.0 | 1000 |
| 5 | H-1 | 1176 | 8.9 | 2.0 | 730 |
| 6 | H-2 | 714 | 9.3 | 1.2 | 280 |

It is apparent from Table 3 that the use of the 1,9-substituted carbazole compound in the light-emitting layer in each of Examples 10 to 18 leads to display of higher luminous characteristics than in other cases (Comparative Examples 4, 5, and 6). Further, good driving life characteristics and high stability are exhibited. This is due to the effects of control of extension of the molecular orbitals and optimization of the balance of electric charges caused by the introduction of a fused-ring substituent composed of two rings or more to the 1 position of carbazole and proves the superior performance of the 1,9-substituted carbazole derivatives. These results clearly indicate that the use of the aforementioned carbazole compounds in the light-emitting layer realizes organic EL devices of high efficiency.

INDUSTRIAL APPLICABILITY

The organic EL device of this invention satisfies a level of performance required for practical use with respect to the luminous characteristics, driving life, and durability and is of high technical value because of its potential applicability to flat panel displays (cellular phone display devices, vehicle-mounted display devices, office computer display devices, and television sets), light sources utilizing the characteristics of planar light emitters (illumination, light sources for copying machines, and backlight sources for liquid crystal displays and meters), display boards, and marker lamps.

The invention claimed is:
1. An organic electroluminescent device comprising:
an anode,
a plurality of organic layers, and
a cathode piled one upon another on a substrate,
wherein the plurality of organic layers comprise an organic layer containing a carbazole compound selected from a carbazole compound represented by general formula (1) or (2);

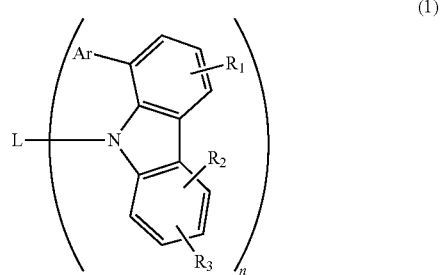

(1)

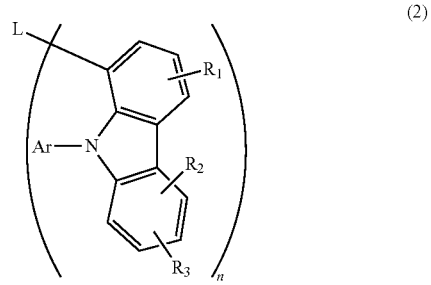

(2)

wherein, in general formulas (1) and (2), each Ar is independently an aromatic group formed by removing 1 to 3 hydrogen atom(s) from an aromatic ring, the aromatic group being selected from aromatic hydrocarbon groups of 6 to 24 carbon atoms and aromatic heterocyclic groups of 3 to 23 carbon atoms; L is an aromatic group formed by removing 1 to 3 hydrogen atom(s) from an aromatic ring, the aromatic group being selected from aromatic hydrocarbon groups of 6 to 30 carbon atoms and aromatic heterocyclic groups of 3 to 30 carbon atoms; each of $R_1$ to $R_3$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms; n is an integer of 1 to 3; when n is 2 or more, a plurality of Ar's or $R_1$ to $R_3$ may be identical with or different from one another, wherein at least one of Ar and L are derived, the former as a monovalent organic group and the latter as an n-valent aromatic group, from an aromatic compound represented by the following general formula (3):

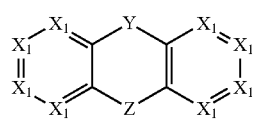
(3)

wherein each $X_1$ is independently $CR_4$ or a nitrogen atom; Y is —O—, —S—, or —$NR_5$—; Z is a direct bond, —O—, —S—, —$NR_6$—, —$CR_7R_8$—, or a group represented by the following formula (Z-1); each of $R_4$ to $R_8$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms; however, the aforementioned aromatic group is a monovalent aromatic group in case it is Ar or an n-valent aromatic group in case it is L

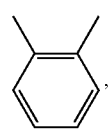
(Z-1)

wherein the carbazole compound has a total of 20 to 80 carbon atoms, and wherein the carbazole compound is co-deposited with a phosphorescent dopant to form a single layer, said single layer being a light-emitting layer.

2. An organic electroluminescent device as described in claim 1 wherein, in general formula (3), Z is a direct bond.

3. An organic electroluminescent device as described in claim 1 wherein either Ar or L is a monovalent or n-valent aromatic group derived from an organic compound represented by the following general formula (4):

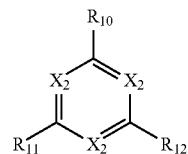
(4)

wherein each $X_2$ is independently $CR_9$ or a nitrogen atom; each of $R_9$ to $R_{12}$ is independently a hydrogen atom, an alkyl group of 1 to 10 carbon atoms, a cycloalkyl group of 3 to 11 carbon atoms, an aromatic hydrocarbon group of 6 to 18 carbon atoms, or an aromatic heterocyclic group of 3 to 17 carbon atoms; however, the aforementioned aromatic group is a monovalent aromatic group in case it is Ar or an n-valent aromatic group in case it is L.

4. An organic electroluminescent device as described in claim 1 wherein light emitted front the phosphorescent dopant has a peak wavelength below 550 nm.

* * * * *